(12) United States Patent
Bowman et al.

(10) Patent No.: US 11,376,014 B2
(45) Date of Patent: Jul. 5, 2022

(54) CATHETER SYSTEM

(71) Applicant: MicroVention, Inc., Aliso Viejo, CA (US)

(72) Inventors: Heath Bowman, Trabuco Canyon, CA (US); Hideo Morita, Irvine, CA (US); Greg Bak-Boychuk, San Clemente, CA (US); Joseph Gulachenski, Trabuco Canyon, CA (US); Arnold Tuason, Claremont, CA (US); Stacy Faught, Aliso Viejo, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 327 days.

(21) Appl. No.: 16/283,663

(22) Filed: Feb. 22, 2019

(65) Prior Publication Data

US 2019/0183513 A1 Jun. 20, 2019

Related U.S. Application Data

(63) Continuation of application No. 15/842,786, filed on Dec. 14, 2017, now Pat. No. 10,265,077, which is a
(Continued)

(51) Int. Cl.
*A61M 31/00* (2006.01)
*A61M 37/00* (2006.01)
(Continued)

(52) U.S. Cl.
CPC .... *A61B 17/12186* (2013.01); *A61B 17/0057* (2013.01); *A61B 17/12031* (2013.01);
(Continued)

(58) Field of Classification Search
CPC .......... A61B 2017/12054; A61B 2017/12063; A61B 2017/12068; A61B 2017/12077; A61B 2017/0065; A61B 2017/12059
See application file for complete search history.

(56) References Cited

U.S. PATENT DOCUMENTS

| 4,655,762 A | 4/1987 | Rogers |
| 6,146,373 A | 11/2000 | Cragg et al. |

(Continued)

FOREIGN PATENT DOCUMENTS

| EP | 1516598 A1 | 3/2005 |
| EP | 2676696 A1 | 12/2013 |

(Continued)

OTHER PUBLICATIONS

Japan Patent Office, Official Action dated Dec. 8, 2020 in Japanese Patent Application Serial No. 2019-221239 with English translation, 7 pages.
(Continued)

*Primary Examiner* — Rebecca E Eisenberg
(74) *Attorney, Agent, or Firm* — Inskeep IP Group, Inc.

(57) ABSTRACT

A catheter with one or more heated or detachable sections is described. The catheter may be useful for liquid embolic delivery, where the heated or detachable sections may help free the catheter when stuck to liquid embolic during delivery. An instrumented catheter is also described.

21 Claims, 21 Drawing Sheets

Related U.S. Application Data continuation of application No. 14/578,020, filed on Dec. 19, 2014, now Pat. No. 9,877,729.

(60) Provisional application No. 61/919,643, filed on Dec. 20, 2013.

(51) Int. Cl.
  *A61B 17/12* (2006.01)
  *A61B 17/00* (2006.01)
  *A61M 25/00* (2006.01)

(52) U.S. Cl.
  CPC ... *A61B 17/12109* (2013.01); *A61M 25/0067* (2013.01); *A61B 17/00491* (2013.01); *A61B 2017/0065* (2013.01); *A61B 2017/00623* (2013.01); *A61B 2017/12054* (2013.01); *A61B 2017/12063* (2013.01); *A61B 2017/12068* (2013.01); *A61B 2017/12077* (2013.01)

(56) References Cited

U.S. PATENT DOCUMENTS

| | | | |
|---|---|---|---|
| 6,296,662 B1 | 10/2001 | Caffey | |
| 6,511,468 B1 | 1/2003 | Cragg et al. | |
| 6,524,274 B1 | 2/2003 | Rosenthal et al. | |
| 6,558,367 B1 | 5/2003 | Cragg et al. | |
| 6,964,657 B2 | 11/2005 | Cragg et al. | |
| 7,896,899 B2 | 3/2011 | Patterson et al. | |
| 7,976,527 B2 | 7/2011 | Cragg et al. | |
| 8,016,799 B2 | 9/2011 | Nash et al. | |
| 8,048,104 B2 | 11/2011 | Monstadt et al. | |
| 8,066,732 B2 | 11/2011 | Paul et al. | |
| 8,066,733 B2 | 11/2011 | Paul et al. | |
| 8,267,955 B2 | 9/2012 | Patterson et al. | |
| 8,454,649 B2 | 6/2013 | Cragg et al. | |
| 8,480,701 B2 | 7/2013 | Monstadt | |
| 8,597,321 B2 | 12/2013 | Monstadt et al. | |
| 8,845,676 B2 | 9/2014 | Monstadt et al. | |
| 2003/0040733 A1 | 2/2003 | Cragg et al. | |
| 2003/0225365 A1 | 12/2003 | Greff et al. | |
| 2003/0225391 A1 | 12/2003 | Cragg et al. | |
| 2004/0225279 A1 | 11/2004 | Raymond | |
| 2006/0229702 A1* | 10/2006 | Agnew | A61F 2/95 623/1.11 |
| 2007/0156117 A1 | 7/2007 | Adams et al. | |
| 2008/0045922 A1 | 2/2008 | Cragg et al. | |
| 2008/0287982 A1 | 11/2008 | Harreld | |
| 2009/0163780 A1 | 6/2009 | Tieu | |
| 2009/0227976 A1 | 9/2009 | Calabria et al. | |
| 2009/0264858 A1 | 10/2009 | Nash et al. | |
| 2010/0049165 A1 | 2/2010 | Sutherland et al. | |
| 2011/0092956 A1 | 4/2011 | Soer et al. | |
| 2011/0264073 A1 | 10/2011 | Cragg et al. | |
| 2011/0319928 A1 | 12/2011 | Griffin et al. | |
| 2012/0157854 A1 | 6/2012 | Kurrus et al. | |
| 2013/0184660 A1 | 7/2013 | Swiss et al. | |
| 2013/0204234 A1 | 8/2013 | Cully | |
| 2013/0211443 A1 | 8/2013 | Cragg et al. | |
| 2013/0338643 A1 | 12/2013 | De Silva | |
| 2014/0039459 A1 | 2/2014 | Folk et al. | |
| 2014/0135737 A1 | 5/2014 | Sutherland et al. | |

FOREIGN PATENT DOCUMENTS

| | | |
|---|---|---|
| JP | 56-43962 A | 4/1981 |
| JP | H07265431 A | 10/1995 |
| JP | 2001509414 A | 7/2001 |
| JP | 2006-181088 A | 7/2006 |
| JP | 2012500102 A | 1/2012 |
| JP | 2013212372 A | 10/2013 |
| WO | WO99/02094 A1 | 1/1999 |
| WO | WO99/62432 A1 | 12/1999 |
| WO | WO2006074060 A2 | 7/2006 |
| WO | WO2008/011626 A1 | 1/2008 |
| WO | WO2010/022180 A1 | 2/2010 |
| WO | WO2012004165 A1 | 1/2012 |

OTHER PUBLICATIONS

Japan Patent Office, Official Action dated Aug. 6, 2019 in Japanese Patent Application Serial No. 2018-089889 with English translation, 4 pages.

Japan Patent Office, Examination Report dated Mar. 27, 2019 in Japanese Patent Application No. 2018-089889, 7 pages.

European Patent Office, Supplementary European Search Report dated Aug. 16, 2017 in European Patent Application No. EP14871037.9, 8 pages.

WIPO, U.S. International Search Authority, International Search Report and Written Opinion dated Apr. 20, 2015 in International Patent Application No. PCT/US2014/071677, 10 pages.

Bormashenko, E. et al., "Electrically Controlled Membranes Exploiting Cassie-Wenzel Wetting Transitions," *Scientific Reports*, 3:3028, Oct. 23, 2013, pp. 5 pages.

\* cited by examiner

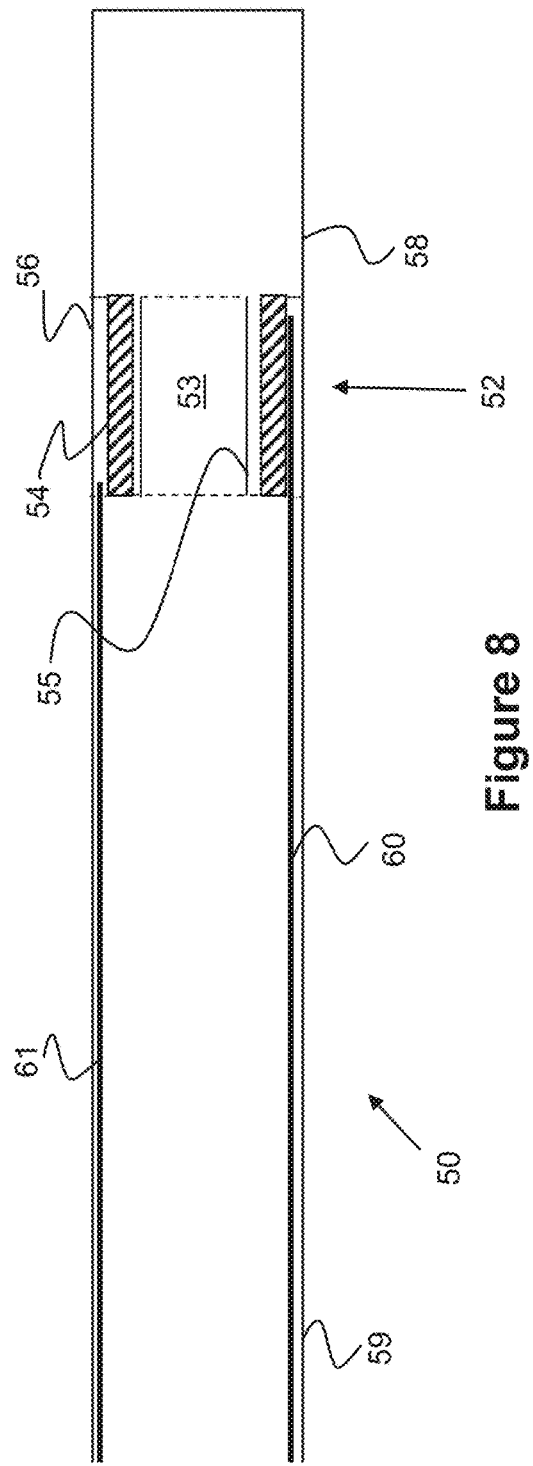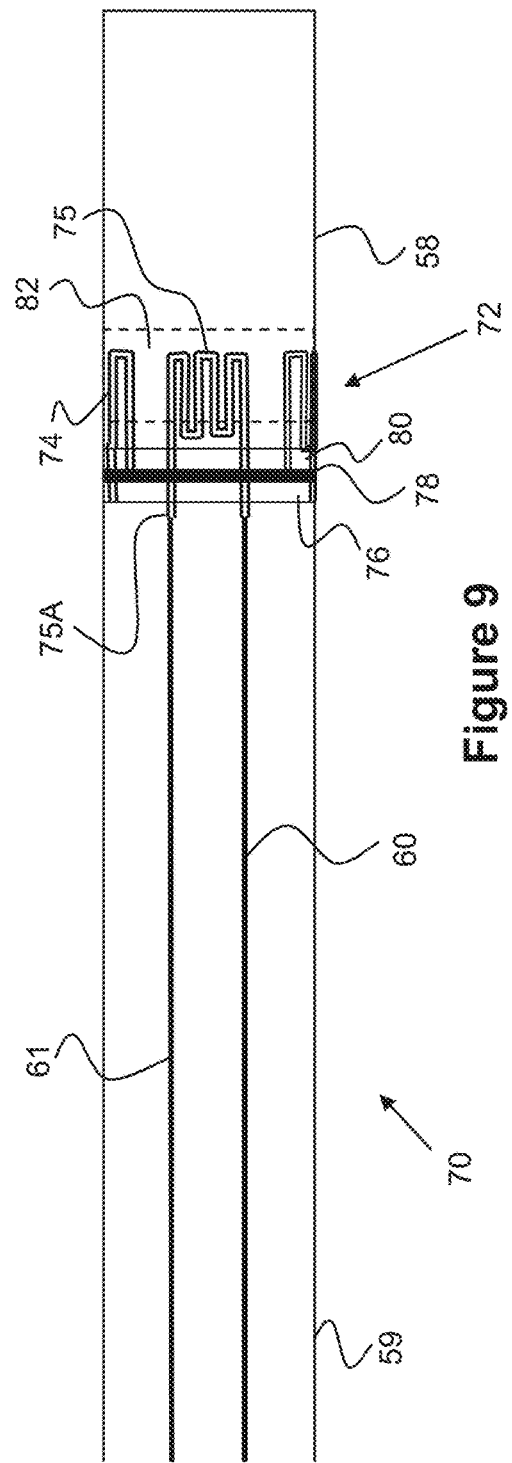

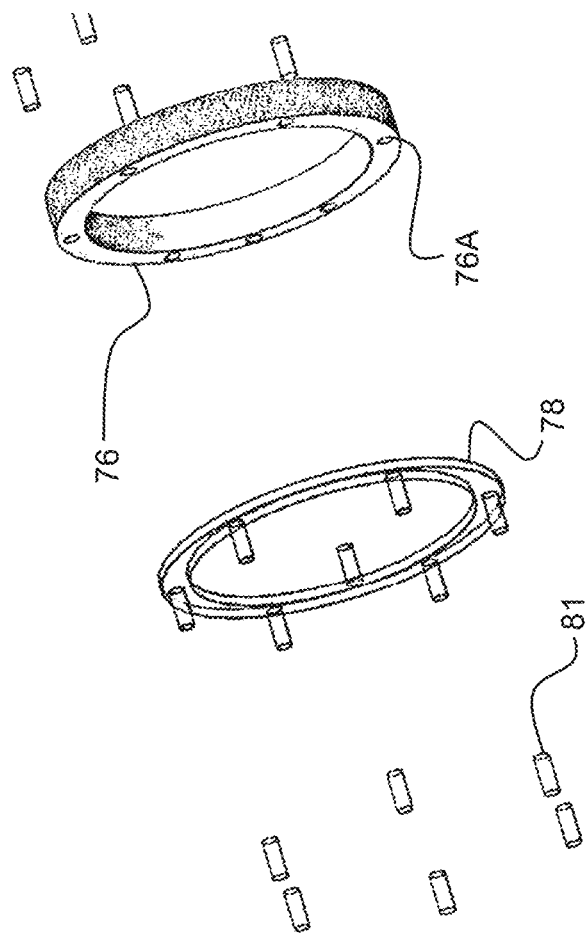
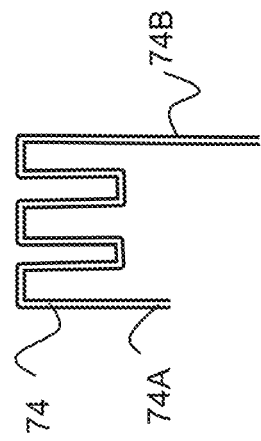
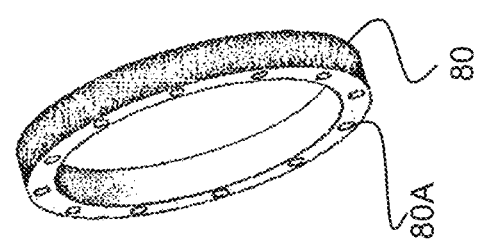
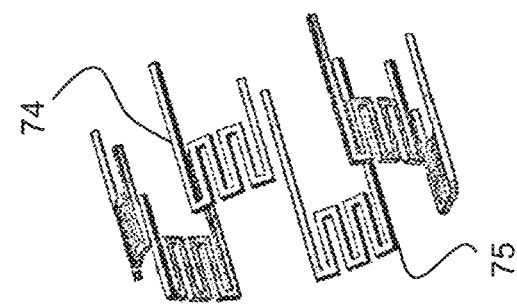

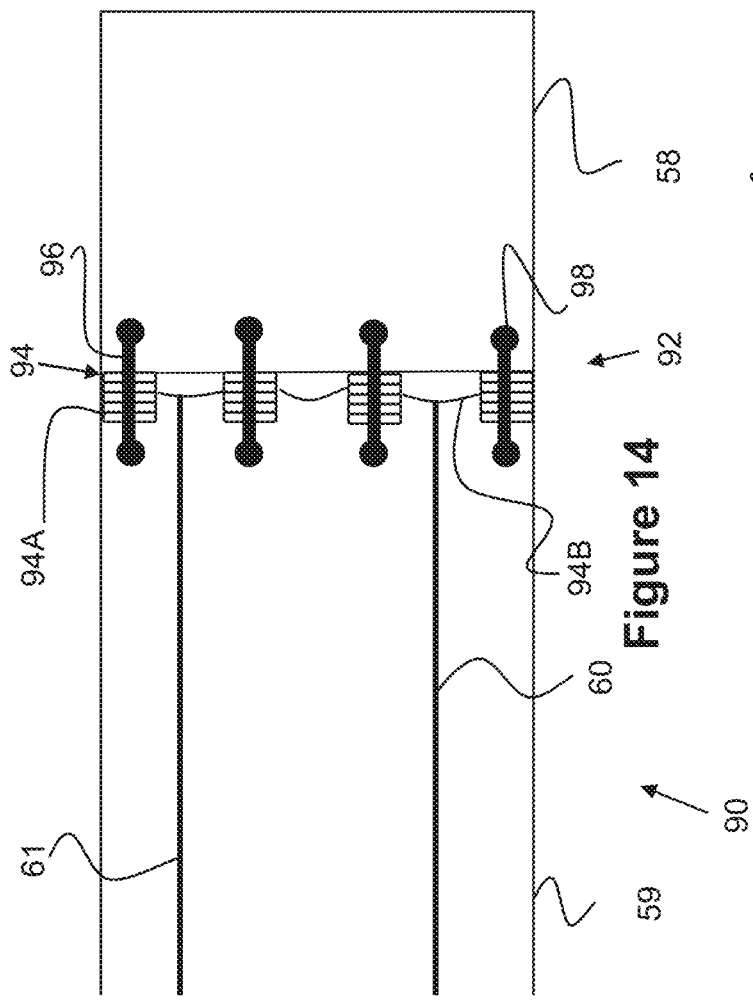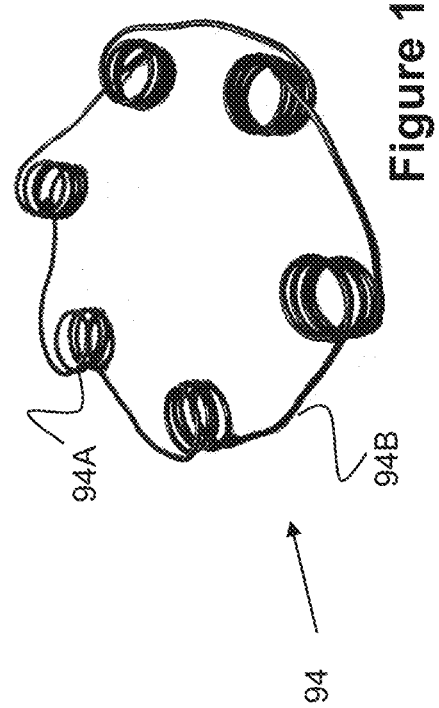

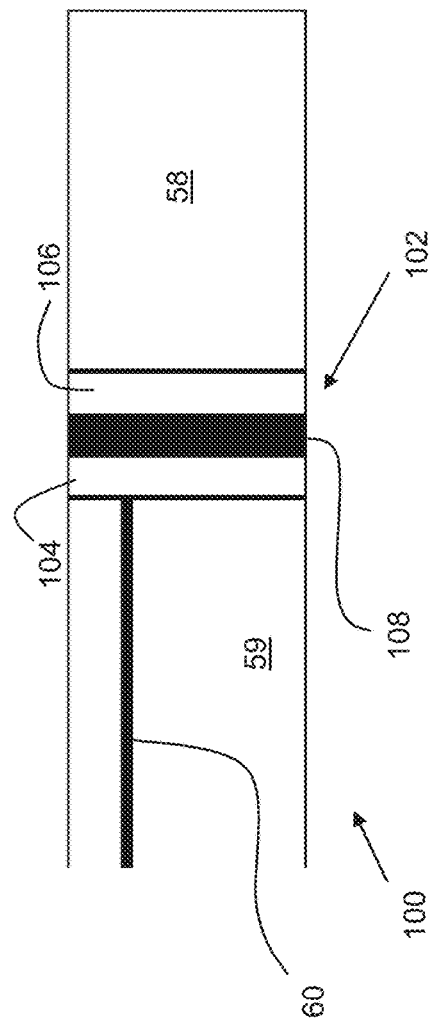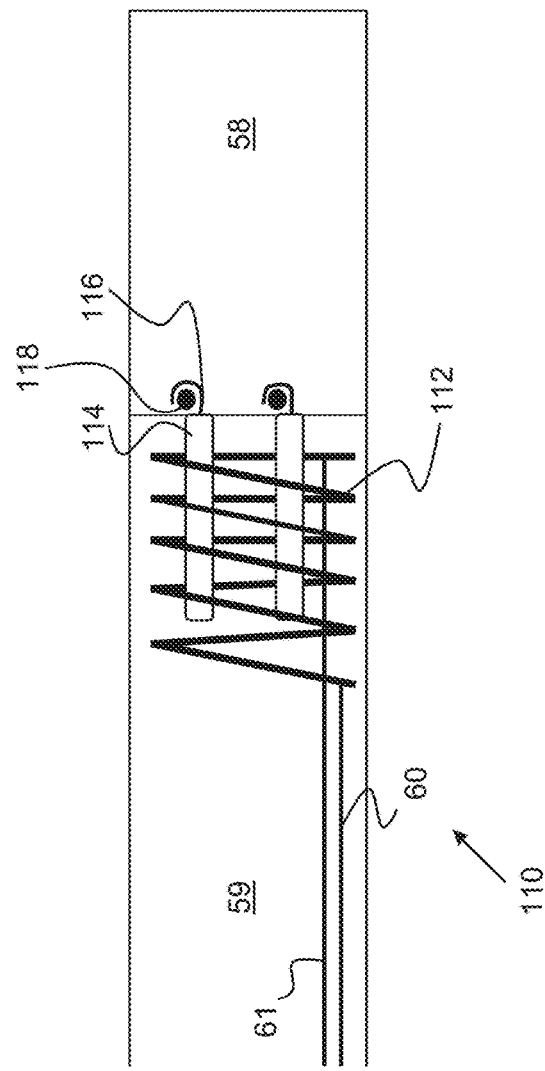

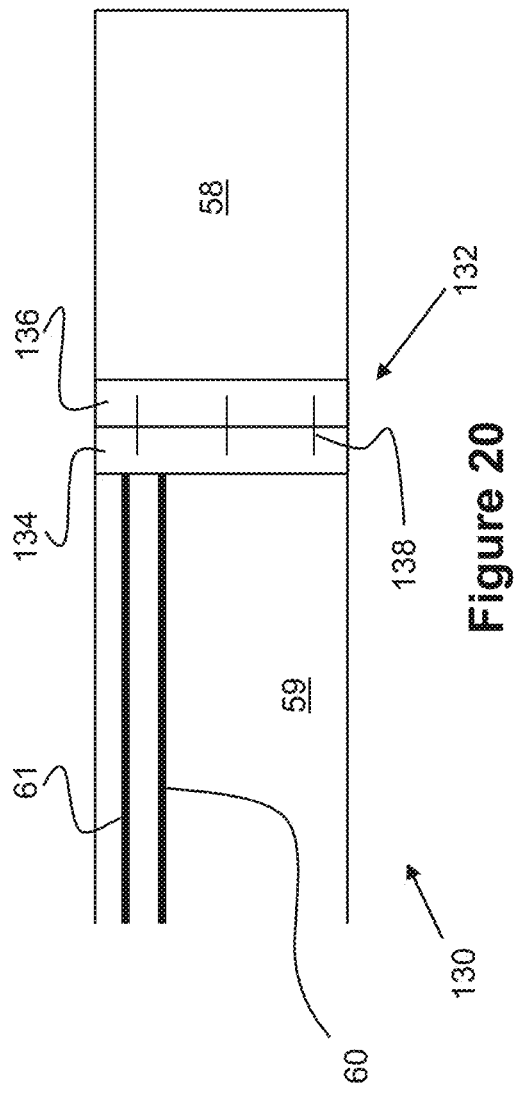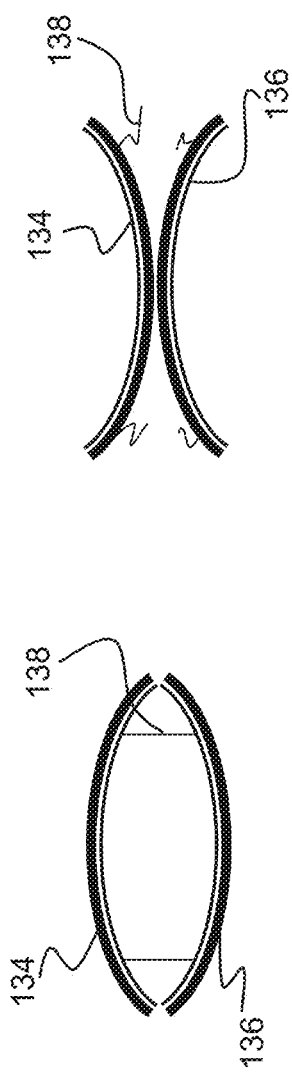

CATHETER SYSTEM

RELATED APPLICATIONS

This application is a continuation of and claims priority to U.S. patent application Ser. No. 15/842,786 filed Dec. 14, 2017 entitled Catheter System, which is a continuation of and claims priority to U.S. patent application Ser. No. 14/578,020 filed Dec. 19, 2014 entitled Catheter System (now U.S. Pat. No. 9,877,729 issued Jan. 30, 2018), which claims benefit of and priority to U.S. Provisional Application Ser. No. 61/919,643 filed Dec. 20, 2013 entitled Catheter System, all of which are hereby incorporated herein by reference in their entireties.

BACKGROUND OF THE INVENTION

Intravascular procedures typically use catheters to deliver a therapeutic agent to the treatment site. Sometimes there may be a danger of the catheter getting stuck at the treatment site. One example is during the delivery of liquid embolic. Liquid embolic can be thought of as a type of biocompatible glue that hardens over time and is used to embolize a particular site within the vasculature. During delivery of the liquid embolic, reflux of the embolic back into the catheter or around the catheter can result in the catheter getting stuck in the vasculature. Thus there is a need for catheters designed with ways to safely and easily extricate the catheter when stuck in the vasculature.

SUMMARY OF THE INVENTION

A catheter with heated or detachable sections is described, where the sections help free the catheter if stuck within embolic material deployed within a patient's vasculature. In one embodiment, a heating device is located at a distal end of the catheter so as to allow a physician to heat the catheter and melt any embolic material that may otherwise be trapping the catheter. In another embodiment, a mechanism is provided to selectively detach a distal end of the catheter, should it become stuck within embolic material deployed within a patient's vasculature.

The present invention contemplates use of any of the embodiments as an embolic delivery catheter, a detachable tip balloon catheter, detachable intrasaccular device, rapid-exchange system that can detach while still on a guidewire, a stent system, a closure device, a neck bridge device, and a coil implant.

In one embodiment, a catheter is disclosed having a heater coil near its distal end.

In one embodiment a catheter includes a conductive trace heater.

In another embodiment a catheter includes a conductive trace heater which is used to melt an adhesive connection to detach a detachable section.

In one embodiment an instrumented catheter utilizes conductive traces as circuit elements which connect to an instrument component along the catheter.

In another embodiment, a catheter is disclosed having a distal end portion connected to a proximal catheter portion via adhesive. A heater coil in the proximate portion can be activated to melt the adhesive and separate the distal portion from the proximal portion.

In another embodiment, a catheter is disclosed having a distal end portion connected to a proximal catheter portion via a bond material that can degrade when exposed to liquid. Exposure of the bond material can be controlled by an electrically controlled Cassie-Wenzel wetting transition material, a film that melts when a heater coil is activated, or a hydrogel layer that shrinks when electric current is applied.

In another embodiment, a catheter is disclosed having a distal end portion connected to a proximal catheter portion via a plurality of tethers or monofilaments. The tethers can be broken by activating one or more heater coils.

In another embodiment, a catheter is disclosed having a distal end portion connected to a proximal catheter portion via a plurality of piston members. When a nearby heater is activated, the pistons actuate, thereby unlocking a locking mechanism on the catheter.

In another embodiment, a catheter is disclosed having a distal end portion connected to a proximal catheter portion via a plurality of tethers of monofilaments. The tethers are connected between two shape-changing components that, when heated, change shape and break the tethers.

In another embodiment, a catheter is disclosed having a distal end portion connected to a proximal catheter portion via a locking mechanism controlled by a temperature sensitive spring member. When heated, the spring member moves, unlocking the locking mechanism, thereby freeing the distal end portion.

In another embodiment, a catheter is disclosed having a distal end portion connected to a proximal catheter portion via a fuse member. When power is applied to the fuse member, the fuse breaks, thereby freeing the distal end portion.

In another embodiment, a method of using a catheter is contemplated. For example, a catheter can be advanced to a treatment site and embolic material can be deployed from the catheter's distal tip. Should the catheter become stuck in the embolic material, the physician can either activate a heater at a distal end of catheter to partially melt the embolic material or activate a detachment mechanism to detach a distal end of the catheter. Finally, the catheter can be removed from the patient.

BRIEF DESCRIPTION OF THE DRAWINGS

FIG. 8 illustrates another embodiment of a catheter having a detachable tip.

FIG. 9 illustrates another embodiment of a catheter having a detachable tip.

FIGS. 10-13 illustrate various components of the detachment system of the catheter of FIG. 9.

FIG. 14 illustrates another embodiment of a catheter having a detachable tip.

FIG. 15 illustrates a heater coil of the detachment system of FIG. 14.

FIG. 16 illustrates another embodiment of a catheter having a detachable tip.

FIGS. 17-18 illustrate another embodiment of a catheter having a detachable tip.

FIG. 20 illustrates another embodiment of a catheter having a detachable tip.

FIGS. 21-22 illustrate cross sectional views of the detachment system of FIG. 20.

DESCRIPTION OF EMBODIMENTS

For the purposes of the Figures described, items on the left are generally considered to sit proximal relative to items on the right and items on the right, in turn, are considered to sit distal relative to items on the left.

Several of the embodiments described utilize conductive traces. Conductive traces are conductive fluids which can be traced over a device, and can be thought of as a conductive ink. The conductive trace is comprised of fine metallic powders amalgamated within a polymer binder. The adhesive properties of the polymer binder allow the conductive trace to be deposited onto a variety of surfaces. When the traces are drawn in a path it provides a conductive, current carrying flow path. They can be used to transfer current between a source and a receiver, and can be integrated into a circuit having (for example) a positive and negative voltage source. See U.S. Pat. Nos. 4,485,387, 7,224,258, 7,736,592 which are hereby incorporated by reference in their entirety. Deposition techniques such as micro-pen, pad printing, bubble jet, screening processes, or rolled deposition during catheter extrusion can be used to deposit the conductive traces on the catheter surface.

Figure 1:
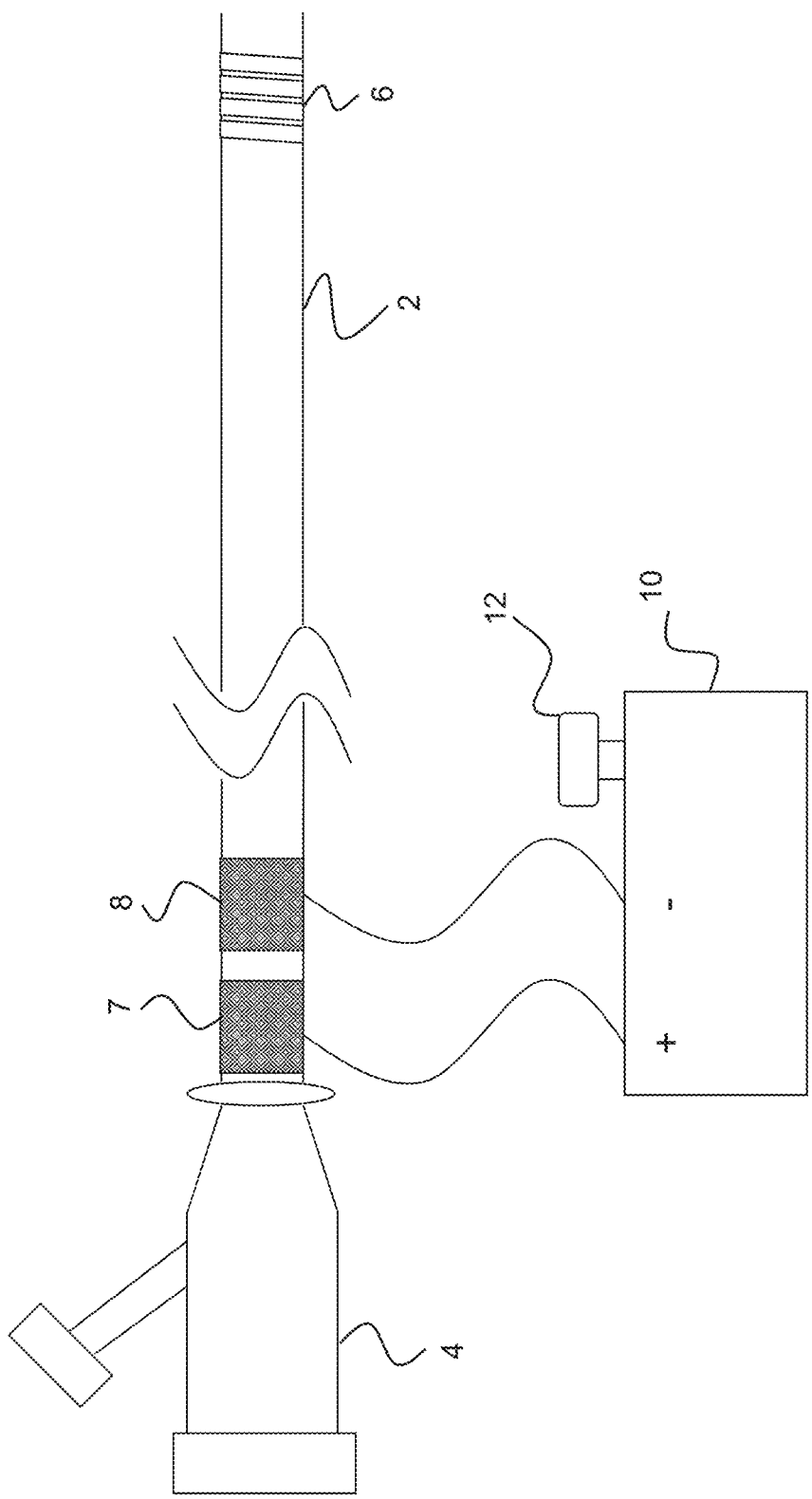
FIG. 1 illustrates a heated catheter system.

FIG. 1 shows a heated catheter system including a catheter 2, y-connector hub 4 at the proximal end of the system, and heater 6 at the distal end of the system. The system further includes proximal contact 7 and distal contact 8 which are connected to a voltage source 10 which includes a user interface, such as a button 12. In FIG. 1 proximal contact 7 is shown as having a positive charge (hooked up to the positive terminal of the voltage source) while distal contact 8 is shown as having a negative charge (hooked up to the negative terminal of the voltage source).

In another example, the polarity of the contacts can be reversed (i.e. proximal contact 7 connected to the negative terminal and distal contact 8 connected to the positive terminal). The button 12 can be engaged to heat the heater 6 by sending electrical current to said heater. In an alternate configuration, the voltage source 10 can sit directly over the contacts 7, 8, physically on the catheter 2. In this configuration the controller can include corresponding terminals and circuitry to interact with contacts 7, 8 on the catheter.

Figure 2:
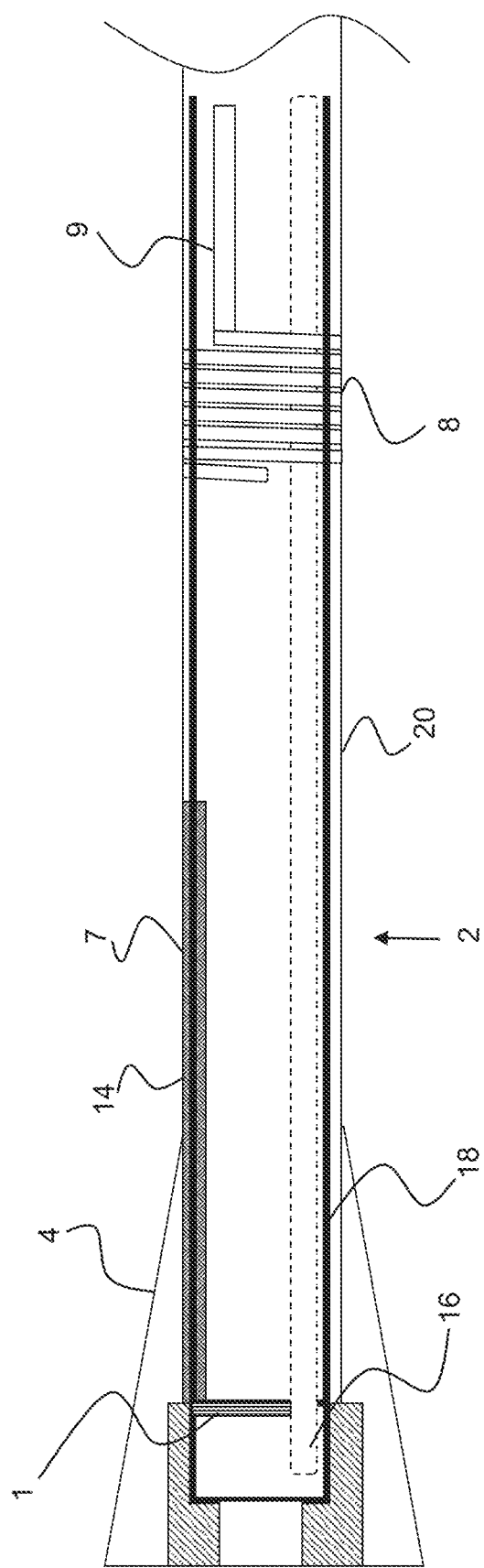
FIG. 2 illustrates a proximal part of a heated catheter system.

FIG. 2 shows a cross sectional view of the proximal end of the system shown in FIG. 1. Catheter 2 is comprised of an inner catheter liner 18 (indicated by the thicker line region) and an outer catheter jacket 20. This inner catheter liner 18 may run through the catheter hub 4 and extends through the rest of the catheter 2. Polymer may be used for both liner 18 and jacket 20, such as PTFE for the inner liner 18 while polyether block amide is used for the outer catheter jacket 20.

The positive terminal of the voltage source connects to proximal contact 7. In one example, proximal contact 7 can be made of a conductive, plated hypotube. This hypotube sits over a conductive trace 16 that runs to the distal portion of the catheter. Conductive trace 16 runs on the inner catheter liner 18. The hypotube can be cemented over the trace, and the cement 14 can be comprised of a conductive epoxy. In one example, as described, the hypotube sits directly over trace 16.

In another example (shown in FIG. 2) the hypotube connects to the trace 16 by the conductive epoxy 14 which acts as a conductive bridge between the two elements. In these configurations the hypotube would sit on the inner catheter layer. In an alternate configuration, a duct can be bore through the outer catheter layer and conductive epoxy can be placed in this duct to provide a current supply between the inner catheter layer and outer catheter jacket. The hypotube can then be placed on the outer catheter surface.

Conductive trace 16 runs along inner liner 18 all the way to the distal portion of the catheter. Distal contact 8 may be formed of a conductive trace fixed over the outer jacket 20 of the catheter 2 and is connected to the negative terminal of the voltage source. As shown in the Figure, part of the conductive trace 9 can form a spiral shape, then extend longitudinally along the length of the catheter 2. In one example, this spiral region is about 1 centimeter in length. Where proximal contact 7 has a positive polarity and distal contact 8 has a negative polarity, trace 16 will act to supply current and trace 9 will act to return current.

Figure 3:
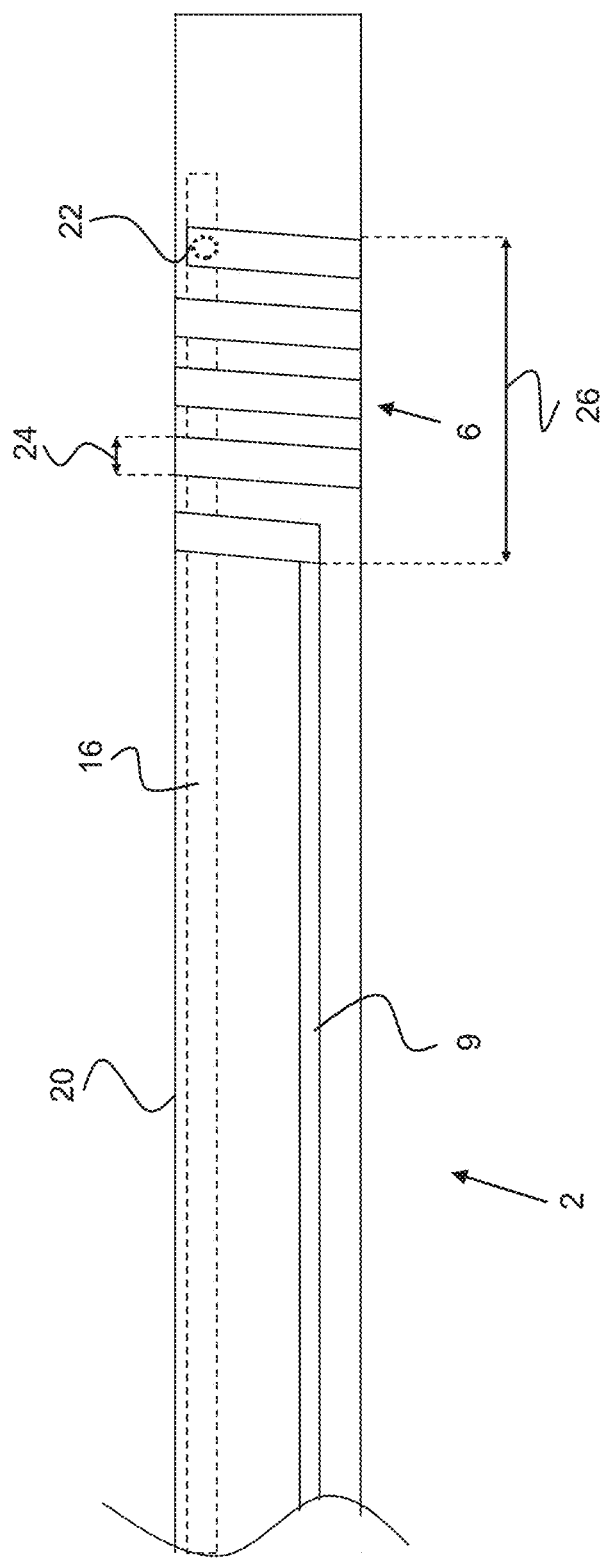
FIG. 3 illustrates a distal part of a heated catheter system, where the system utilizes a heater placed on the outer surface of a catheter.

FIG. 3 shows the distal part of the catheter 2. Conductive trace 16 is located along the inner catheter liner 18 to the distal portion of the catheter 2. For the configuration shown in FIGS. 2 and 3, conductive trace 16 has a positive charge, thus supplying current (though as mentioned earlier the polarity of contacts 7, 8 could be reversed). Conductive trace heater 6 is located over the outer jacket 20 of the catheter 2 in a spiral shape at the distal part of the catheter. The tight spiral configuration promotes heat generation as current passes through, due to the close travel path of the current through the spiral and the increased resistance through this section.

At the end of the spiral/coiled configuration 6, conductive trace 9 extends longitudinally along the catheter 2. Trace 9 extends proximally back to the distal contact 8 shown in FIG. 2. In one example, the trace width 24 of the windings of the heater 6 can be about 0.002" to 0.005". In one example, the heater length 26 can be about 1 to 2 cm. In one example, a current of at least 200 milliamps is desired for the heater coil 6. Trace width, heater length, and conductive material used in the conductive trace are variables which may affect the heater current. In one example, the heater winding width 24 is thinner than the supply and return trace conductors 9 and 16 so that the resistance of heater 6 will be higher than the resistance of the supply and return trace 9 and 16.

To connect conductive trace 16 and heater 6, a duct 22 is bore through the outer catheter jacket 20. Conductive epoxy can be placed through this duct to connect trace 16 to heater 6, thus providing a current path from trace 16 (which sits on the inner catheter liner 18) to heater 6 (which sits on the outer catheter jacket 20). Where proximal contact 7 is positive and distal contact 8 is negative, the current flows from proximal contact 7 to conductive epoxy 14 to conductive trace 16 all the way to the distal portion of the catheter. The current then flows through the conductive epoxy 14, through duct 22 to heater 6, then through conductive trace 9 and back to the distal contact 8.

A user can initiate heating of heater 6 by pressing the button 12 on voltage source 10 to activate an electric pulse. The current pulse will then travel through the system in the manner just specified. In one example the DC electrical pulse from the controller will have a regulated current output and pulse duration (i.e. between 0.5-3 seconds). In one example the pulse duration is tuned such that the transient heating effect at the surface of the catheter heating element 6 does not exceed about 165 degrees F. In another example an alternating current voltage source is used.

Though a voltage source 10 is described, this device can include a controller system which contains a voltage source and impulse mechanism (button 12). U.S. Pat. No. 8,182,506 and US20060200192, which are hereby incorporated by reference in their entirety, describe implant detachment systems utilizing such a controller. The controllers described in those references may be used in the system/systems described in this document. In one example voltage source 10 can use a 9 Volt battery. In another example one or more 3 Volt batteries can be used. In another example multiple 9 Volt batteries can be used. In another example three 3 Volt batteries can be used. The voltage source may sit proximal of catheter hub 4, as a handheld unit for the user. Alternatively the voltage source may sit just distal of the catheter hub, mounted on the catheter. In this configuration the controller can include corresponding terminals and circuitry to interact with contacts 7, 8 on the catheter.

In another embodiment the heater 6 may be a metallic heater coil. A conductive epoxy may be used to connect the heater coil to the conductive trace 9.

Figure 4:
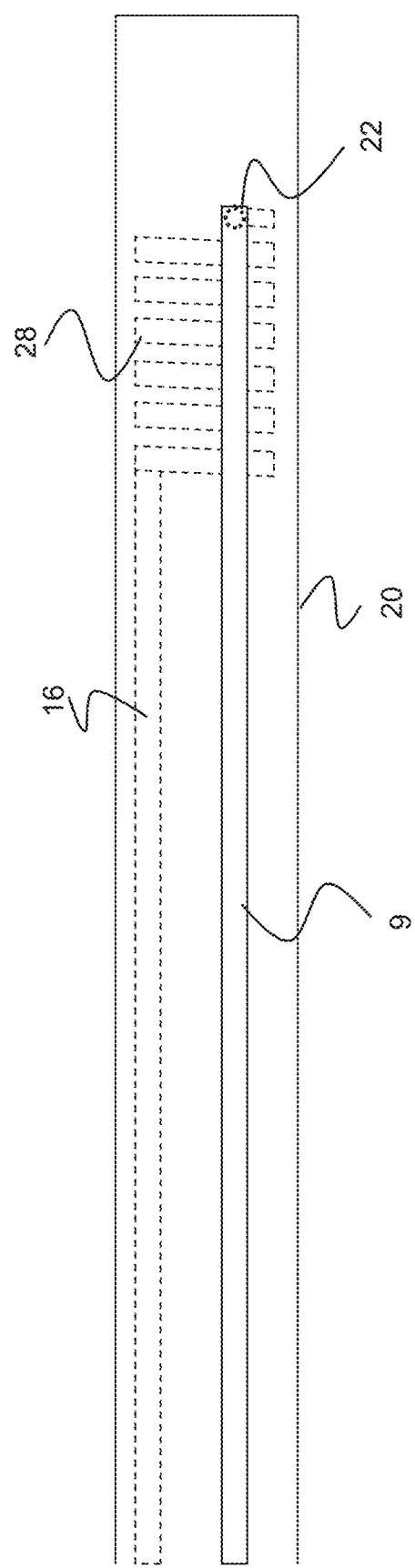
FIG. 4 illustrates a distal part of another embodiment of a heated catheter system.

FIG. 4 illustrates an embodiment of a heated catheter system that is generally similar to the previously described embodiment of FIGS. 1-3. The conductive trace 16 is located on the inner catheter layer connects to a metallic heater coil 28, which also is located on the inner catheter layer. In one example, conductive epoxy is used to connect element 16 to coil 28. This coil 28 extends along a distal portion of the catheter. Duct 22 is present at the distal portion of coil 28 and is formed from a passage or bore through the outer jacket 20 of the catheter. Trace 9 is located on the outer surface of the jacket 20 and is connected to the coil 28 by conductive epoxy within duct 22. The current path (assuming trace 16 is connected to a positive terminal and trace 9 to a negative terminal) runs from proximal contact 7 to conductive epoxy 14 to conductive trace 16 to coil 28, all elements being on the inner catheter layer. The current then travels through the conductive epoxy in duct 22 to return trace 9 back to the distal contact 8, where trace 9 and distal contact 8 are located on the outer catheter jacket.

In the embodiments presented above, conductive epoxy is described as a bridging mechanism to provide a conductive path between elements, and/or between elements on different layers of the catheter. Other conductive materials besides epoxy may be used.

The heated catheter embodiments presented in FIGS. 1-4 may be useful for situations where the embolic hardens around the external surface of the catheter, thus trapping the catheter within the vasculature. The heater works to melt the embolic thus allowing the catheter to be freed. The heaters discussed could be utilized at multiple places along the length of the catheter as well.

Generally a solid metallic material (i.e. a heater coil) will have a higher operating temperature than a conductive trace, since the conductive trace can only operate as a heater up to the melting point of the trace. The conductive trace, however, takes up less space on the catheter versus a solid hypotube or coil thus reducing the overall profile of the catheter and reducing the stiffness of said catheter compared to a catheter utilizing a solid metallic material. Thus for the embodiment shown in FIG. 3 where the heater is on the outside of the catheter a conductive trace may be sufficient to melt any embolic stuck on the outside of the catheter. For the embodiment in FIG. 4, where the heater is placed on the inner catheter layer, any heat generated must transfer through the outer catheter layer before it can begin to melt the embolic in contact with the catheter. Thus a heater which can reach a higher temperature (i.e. the metallic heater coil) may be desirable.

Many catheter designs utilize coils to provide structural stability to the catheter as it navigates the vasculature. Thus the heater coil embodiments described herein can be utilized in a catheter already utilizing a coil or metallic layer for structural reinforcement. The various circuitry elements (conductive traces and/or conductive hypotubes and the like) can thus be combined with an existing structural coil element to create a heater coil. Similarly, a heater coil could provide heat as well as structural stability to a catheter.

Figure 5:
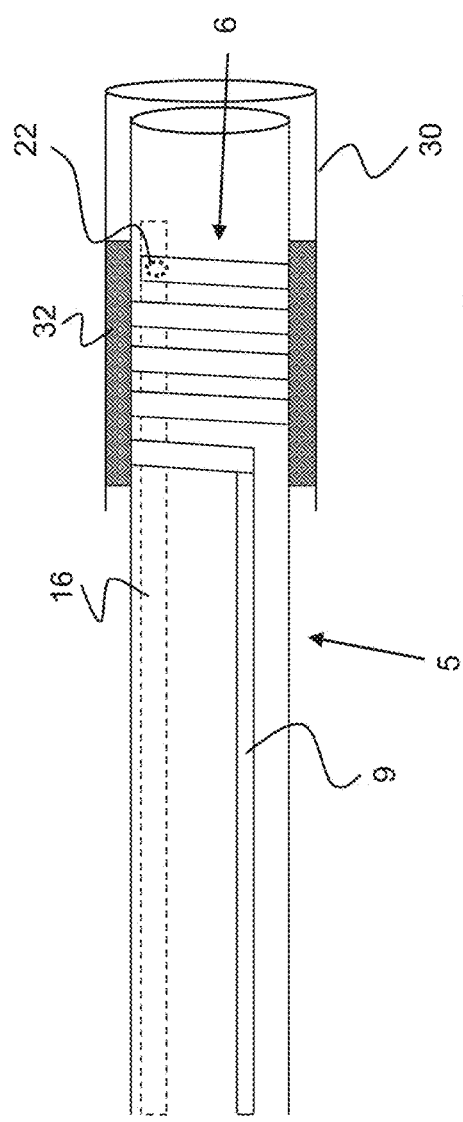
FIGS. 5-6 illustrate a detachable catheter section utilizing an adhesive and a heater.
Figure 6:
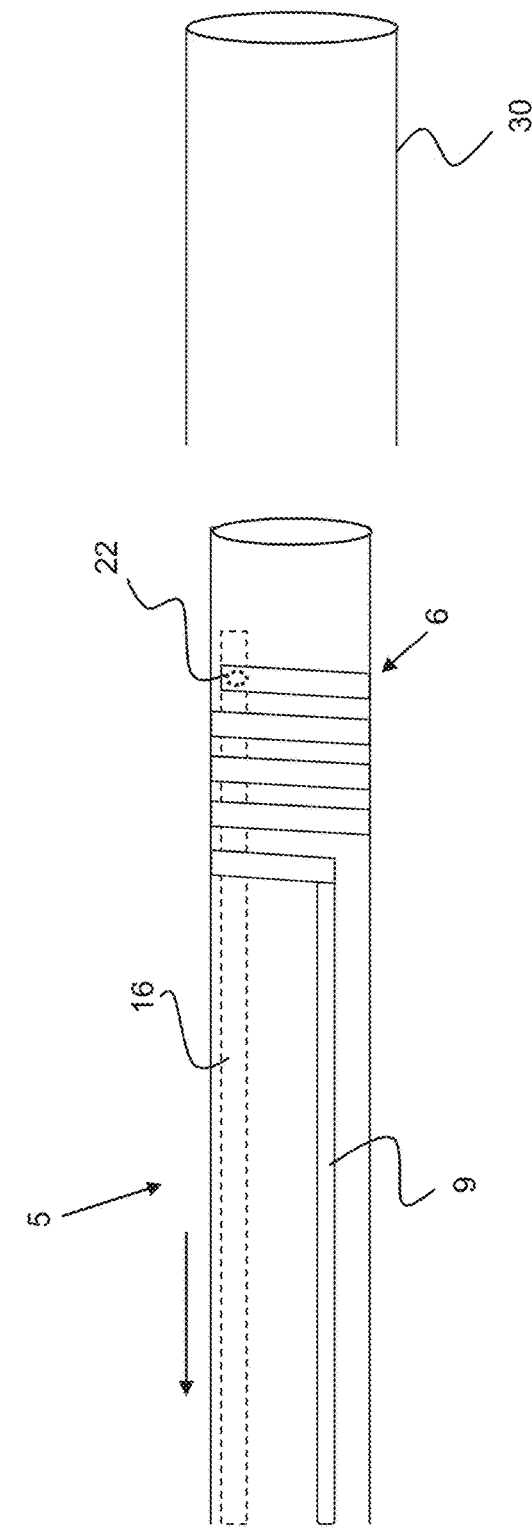

FIGS. 5-6 show another embodiment of a heated catheter 5 which utilizes a distal, detachable tubular section 30 that fits over the distal end of the main body of the catheter 5 and can be disconnected by activation of heater 6. As the heater is activated, the section 30 expands in diameter, breaking the adhesive 32. Preferably, section 30 is connected to a distal end portion of the catheter 5 via adhesive 32. If the distal, detachable section 30 gets stuck during embolic delivery, it can be detached and left within the embolic material in the patient while the remaining portion of the catheter 5 is removed. In one example, the heater 6 utilizes a conductive trace and reaches to a temperature between about 120-160 degrees F. In one example, a metallic heater coil is used as the heater 6. The adhesive 32 ideally has a relatively low melt temperature (e.g., about 120-160 degrees F.).

Another embodiment contemplated would utilize a metallic heater coil for heater 6. A detachable section 30 is included; however, no adhesive is used. Instead, a shrink tube (e.g., cross-link polyolefin) made of very soft material is placed over the heater coil. In one example the durometer for this shrink tube is less than 30D. Due to the softness of the material it will conform to the surface of the metallic heater coil, and adhere to the coil especially as the coil generates heat.

Detachable section 30 is preferably has a tubular shape that is initially slightly larger than the catheter's diameter. The section 30 is placed over the shrink tube and preferably has a high degree of shape memory. A high degree of shape memory can be imparted to the detachable section by utilizing a high area draw-down ratio. Draw down ratio is the ratio of the cross sectional area of the extruded plastic melt to the cross section area of the final product. A high draw down ratio means a significant difference between the two areas, meaning the final product (the detachable section) will retain a high degree of shape memory, retained from the higher pre-processed cross sectional area. As the detachable section is heated from the underlying heater coil, the detachable section will return to its expanded preset shape memory shape, thus detaching from the coil and shrink tube. In an alternative configuration, no shrink tube is utilized and the detachable section directly overlies the heater coil.

Elements 9 and 16, as in the previous embodiments, can be made of a conductive trace. In one example, trace 9 is on the inner catheter liner surface and trace 16 is on the outer jacket. In another example both traces sit on the inner catheter liner surface. In another example both traces sit on the outer catheter jacket. In one example, these traces sit external of the outer catheter jacket. In another example, one or more of the traces may run through the catheter. Alternatively, conductive plated hypotubes can be used. Alternately, conductive wires can be used. When the heater generates heat, the generated heat will cause the detachable section to expand (the inner diameter will expand while the length contracts) until it detaches from the heater and shrink tubing overlying the heater. The shrink tubing stays with the heater due to the softness and conformity of the tubing. When detachable section 30 completely detaches the rest of the catheter can be pulled away, thus leaving detachable section 30 with the embolic mass.

Figure 7:
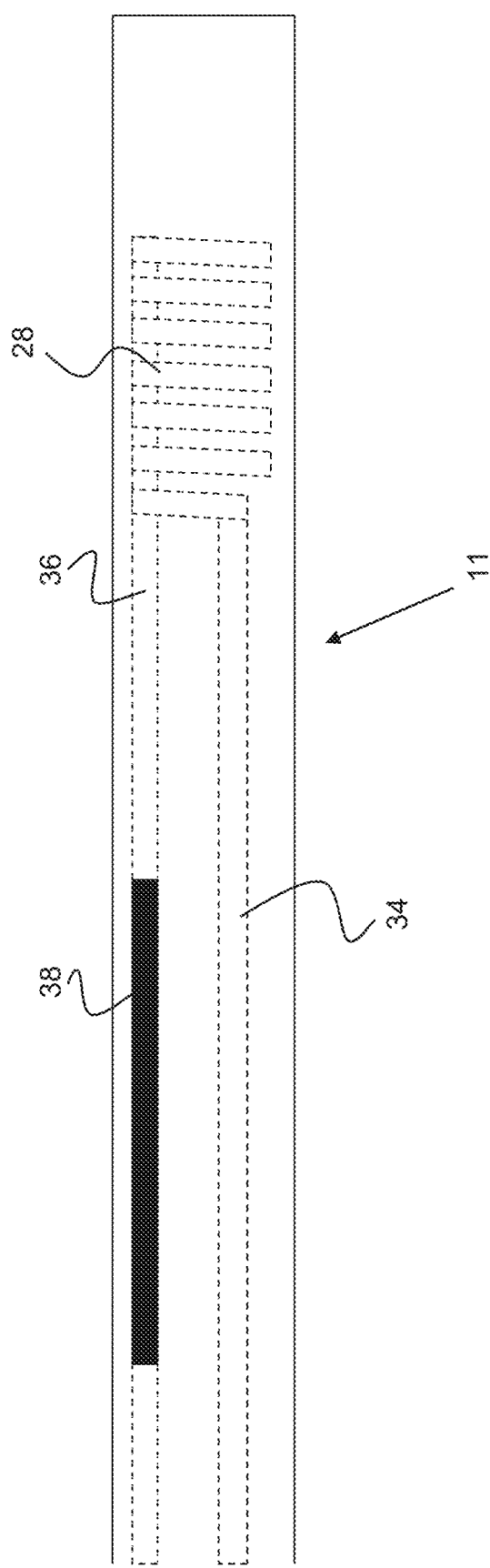
FIG. 7 illustrates another embodiment of a heated catheter system.

FIG. 7 shows another embodiment of a catheter 11 utilizing a coil 28 that acts as both a structural element and a heater. The conductive traces/circuitry described could be utilized with structural coils to create a heater coil which also promotes structural integrity of the catheter. Conductive traces 34, 36 are located on the inner catheter liner 18. For the purpose of example, trace 34 is the supply current (positively polarized) and trace 36 is the return current (negatively polarized). Return trace 36 is insulated by a non-conductive material 38 on top of the trace 36 for most of its length, but leaves exposed a distal portion of the conductive trace 36. Coil 28 is wound over the inner liner 18 and is connected to trace 34, 36. The outer catheter jacket 20 is positioned over the inner layer 18 and coil 28, and the layers are fused together via application of elevated temperatures and compression. The fusing action serves to interconnect the trace to the coil 28, thus eliminating any need for additional electric interconnections.

The coil 28 can act as a heater due to the connection to the traces which are, in turn, connected to a voltage source. The coil 28, being on the inner layer 18 of the catheter 11, provides both structural stability to the catheter and acts as a heater. If the distal portion of the catheter 11 is stuck to an embolic mass, the heater 28 can be activated melting any liquid embolic at the surface of the catheter 11, thus helping to free the catheter 11.

The metallic heater coils discussed herein, in one example, may be made of a highly electrically resistive material to increase the resistance of current as it travels through the coil, thus increasing the coil temperature. Factors such as the desired temperature range would impact material selection. Temperature is an important factor in material selection since one would want a temperature high enough to melt embolic but not high enough to melt the actual polymeric material used in the catheter.

The embodiments described in FIGS. 2-4 and 7 utilize a heating element heating a portion of the catheter to melt embolic and the requisite circuitry (i.e. conductive traces) that can be used to convey current to the heating element. This technology can be used for a number of similar applications. In another embodiment, the conductive traces may be used to ferry current to a sensor (i.e. a temperature sensors or pressure sensor), where said sensor takes the place of the heating element. The conductive traces as described earlier can be used to provide a current flow path to the sensor. Thus one could create an instrumented catheter that is capable of measuring temperature and/or pressure, which has minimal stiffness due to the conductive trace circuit elements.

Several embodiments described utilize conductive traces as circuitry elements. Different embodiments could utilize various conductive elements (conductive hypotubes, wired circuit elements, etc.) to replace these conductive traces. Alternatively, the various conductive elements (conductive hypotubes, wired circuit elements, etc.) could be used in combination with the conductive trace.

FIG. 8 illustrates another embodiment of a catheter 50 having a detachable tip 58. The catheter 50 includes a detachment joint 52 that connects the proximal portion 59 of the catheter 50 with the distal tip portion 58. The detachment joint 52 is held together with a bond material 54 that can degrade (chemically or otherwise) when exposed to liquid such as blood, contrast, saline, or other commonly injected interventional fluids. For example, the bond material 54 may include a salt such as NaCl or similar salts that can dissociate into solution when exposed to liquid.

In one example, the bond material 54 can be selectively exposed to liquid via an outer electrically controlled membrane 56. When current is applied via electrical wires 60 and 61, the membrane allows fluid to enter the joint 52, allowing the bond material 54 (e.g., NaCl) to go into solution and the distal tip portion 58 to separate from the proximal catheter portion 59. In one example, the outer membrane 56 operates via the Cassie-Wenzel wetting transitions effect, which is described in Bormashenko, Edward, Roman Pogreb, Sagi Balter, and Doron Aurbach. "Electrically Controlled Membranes Exploiting Cassie-Wenzel Wetting Transitions." *Scientific Reports* 3 (2013), the contents of which are hereby incorporated herein by reference.

In another example, outer membrane portion 56 can be a layer of hydrogel that, when an electric current is passed through via wires 60 and 61, causes the hydrogel to give off fluid itself and shrink. Once sufficiently shrunken, the hydrogel will allow fluid from outside the catheter 50 to enter the joint 52 and degrade the bond material 54. In one embodiment, the hydrogel alone is used. In another embodiment, the hydrogel has a permeable film or layer over it.

In another example, the outer membrane 56 may be a thin film that melts or degrades when current from the electrical wires 60 and 61 are applied to it. For example, this film could be composed of a polymer such as polyurethane or polyolefin with a melting point sufficient to melt via activation of the heater.

In alternate embodiments, the inner surface 55 of the joint 52 could be configured to selectively allow passage of fluid (e.g., saline or contrast) from the inner passage 53 to the bond material 54. This selective passage of fluid can be accomplished via any of the mechanisms discussed with regard to outer member 56, and can be used alone or in addition to the outer membrane 56 (i.e., both membranes can selectively allow passage of fluid).

FIGS. 9-13 illustrate various aspects of a catheter 70 having proximal portion 59 and distal portion 58 that is detachable via joint 72. Generally, the joint 72 includes a plurality of heating elements 74 and 75 attached to the proximal portion 59 of the catheter that, when activated, melt adhesive members 84, thereby releasing the distal portion 58.

Figure 10:
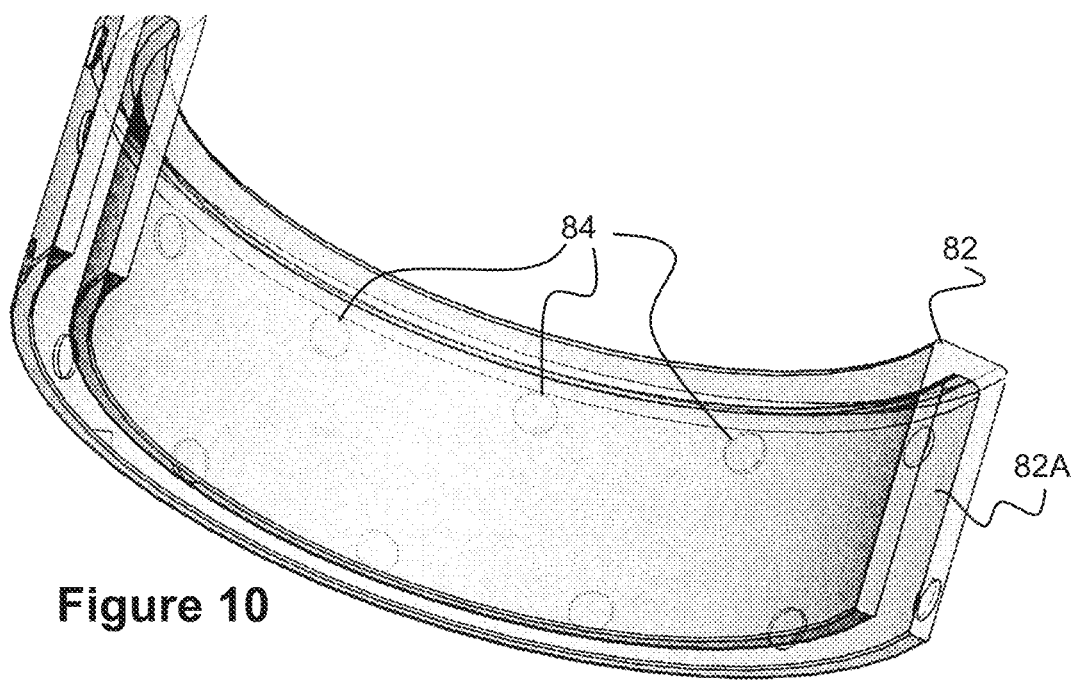
Figure 11:
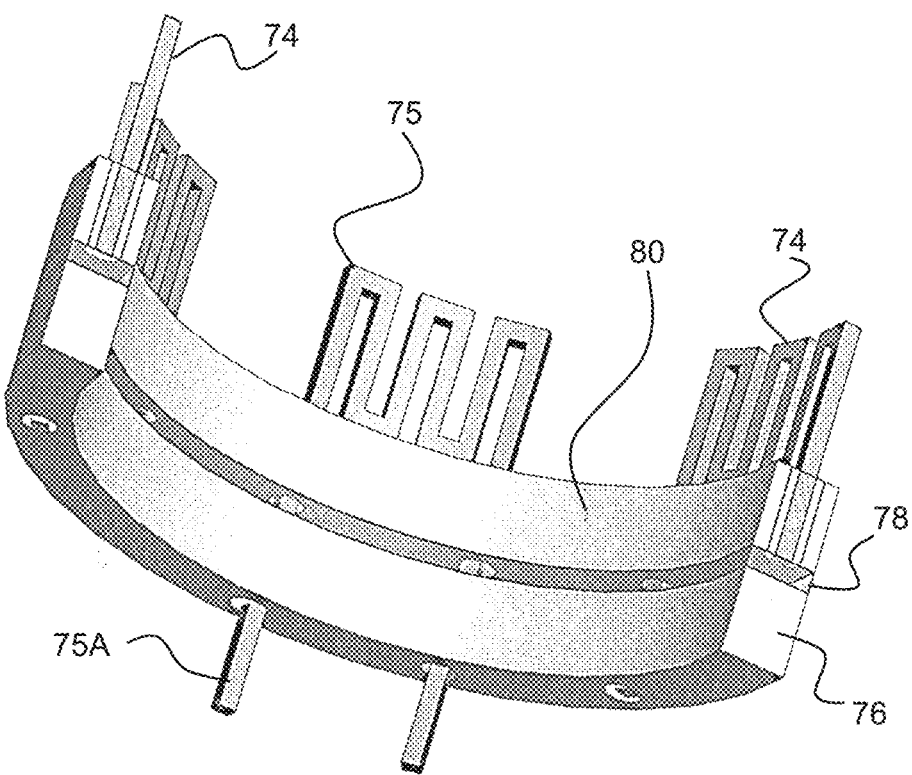

As best seen in FIG. 10, the adhesive members 84 are located within a groove 82A of a distal ring 82, which is fixed to the distal catheter portion 58. The heating elements 74 and 75 are also positioned in the groove 82A, such that the adhesive members 84 fix or secure the heating elements 74 and 75 to the distal ring 82, thereby maintaining the distal catheter portion 58 with the proximal catheter portion 59.

In one embodiment, the heating elements 74 and 75 form a plurality of generally rectangular shapes, though a variety of different shapes are possible, such as a single square or a plurality of circular loops.

Electrical current is distributed to each of the heating elements 74 and 75 via a distal conductive ring 80 and a proximal conductive ring 76. At least one heating element 75 includes elongated proximal ends that pass entirely through the rings 76 and 80 (as well as the insulating layer 78 located between the rings 76, 80). One of the ends 75A connects to electrical wire 60, while the other end 75A connects to electrical wire 61, allowing the element 75 to be selectively supplied with power. One of the elongated proximal ends 75A is in electrical contact with proximal ring 76, while being insulated from electrical contact with distal ring 80. The other proximal end 75A is in electrical contact with distal ring 80, while being insulated from electrical contact with proximal ring 76. In this respect, the ends 75A provide a path for current to and between the rings 76 and 80.

The remaining heating elements 74 preferably have a first end 74A that makes electrical contact with only the distal ring 80 and second end 74B that makes electrical contact with only the proximal ring 76. As seen in FIGS. 12 and 13, this arrangement can be accomplished by the first end 74A having a relatively small length that permits entry into only one of the apertures 80A of the distal ring 80, and the second end 74B having a relatively long length that extends through aperture 80, through the apertures of the insulating layer 78, and into one of the apertures 76A of the proximal ring 76. Insulating members 81 can be further located on portions of the second end 74B located within the aperture 80A of the distal ring 80, thereby preventing electrical contact that would otherwise prevent current from flowing completely through the heating element 74.

FIG. 14 illustrates another embodiment of a catheter 90 with a distal portion 58 that detaches from a proximal portion 59, via joint 92. The joint 92 is held together by a plurality of tethers or monofilaments 96 located axially and circumferentially around the wall of the catheter 90. Each tether 96 is anchored under tension to both the distal portion 58 and the proximal portion 59 via anchors 98. The anchors can be an adhesive, bonding agent, a distinct element that the tether 96 can be tied to, or similar fastening mechanisms.

The tethers 96 are preferably broken by a resistive heater located near each of the tethers 96. For example, FIGS. 14 and 15 illustrate a resistive heater ring 94 that is composed of a plurality of coiled portions 94A connected by adjacent curved regions 94B, so as to form a ring shape. Each of the coiled portions 94A are preferably coiled around one of the tether members 96, so as to allow efficient heat transfer to the tether members 96. Finally, electric wires 60 and 61 selectively apply current to the ring 94, causing the coils 94A to heat up and melt or break the tether members 96 and release the distal portion 58 of the catheter 90 from the proximal portion 59.

FIG. 16 illustrates another embodiment of a catheter 100 having a tip portion 58 that detaches from a proximal portion 59 via an electrolytic joint 102. Specifically, the joint 102 preferably contains a proximal ring 104 and a distal ring 106 that are in contact with a middle sacrificial anode ring 108. Electric wire 60 provides positive current to the ring 104, while negative current is supplied via fluid from within the catheter 100 or through the patient's blood via an electrode in contact with the patient. The rings 104, 106 and the middle sacrificial anode ring 108 are selected so as to cause rapid galvanic corrosion of the anode ring 108 (i.e., the anode ring 108 acts as an anode and the rings 104, 106 act as a cathode). Once the anode ring 108 has sufficiently corroded, the distal portion 58 of the catheter (including ring 106) disconnect from the proximal portion 59.

Figure 18:
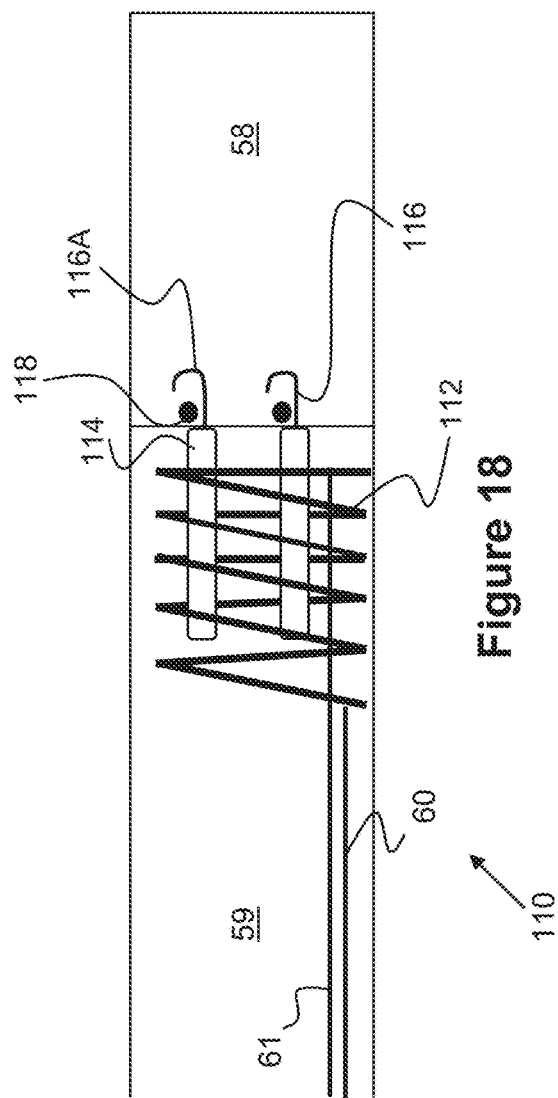
Figure 19:
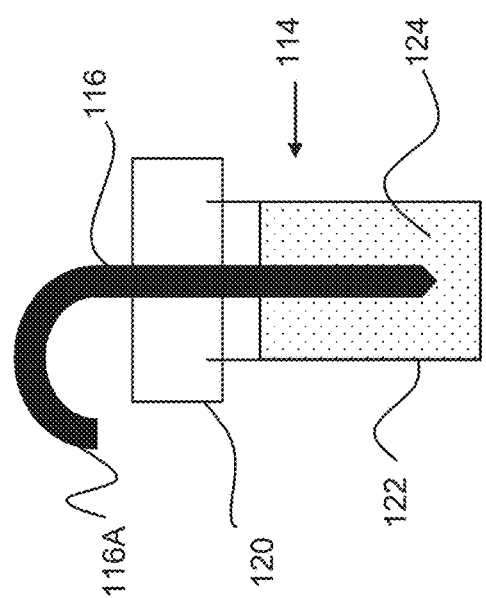
FIG. 19 illustrates a piston member of the detachment system of the catheter from FIGS. 17-18.
Figure 23:
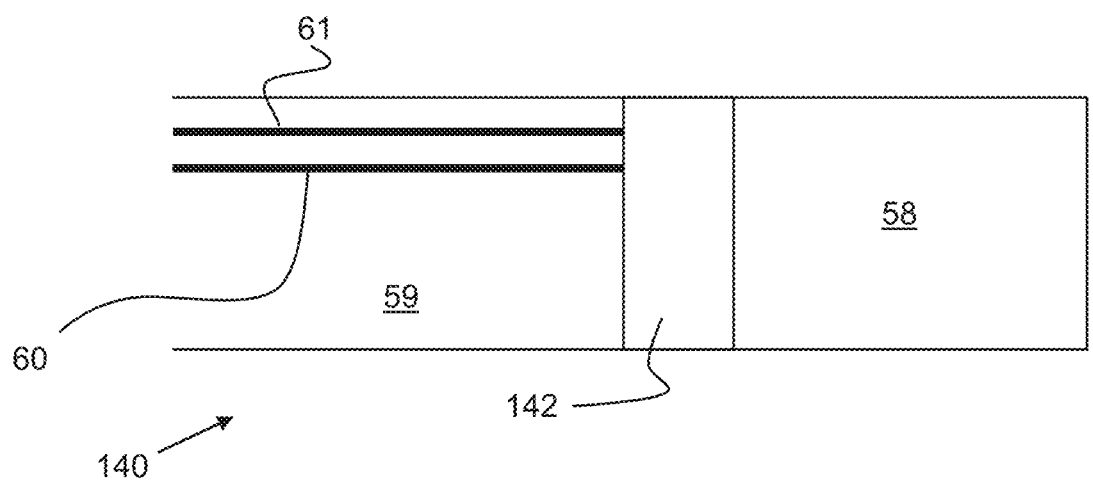
FIG. 23 illustrates another embodiment of a catheter having a detachable tip.
Figure 24:
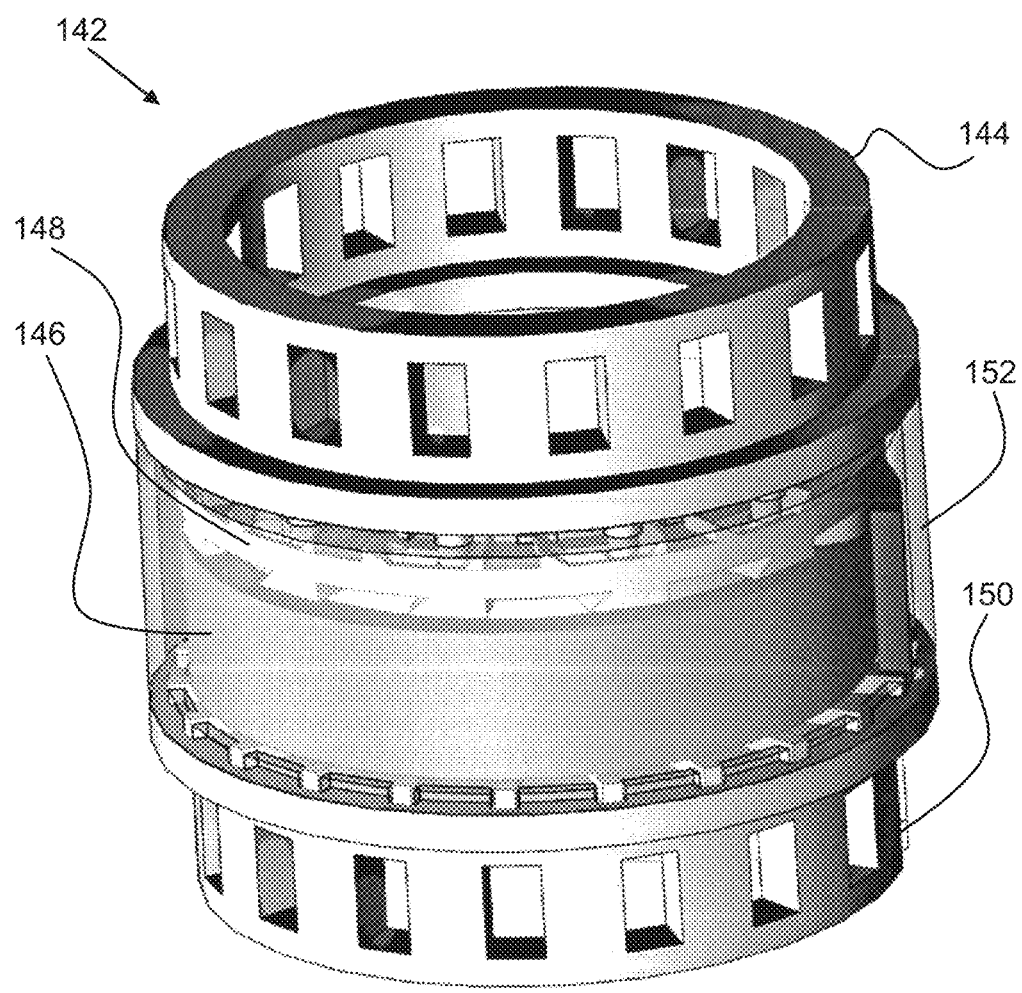
FIGS. 24-33 illustrate various components of the detachment system from the catheter of FIG. 23.
Figure 25:
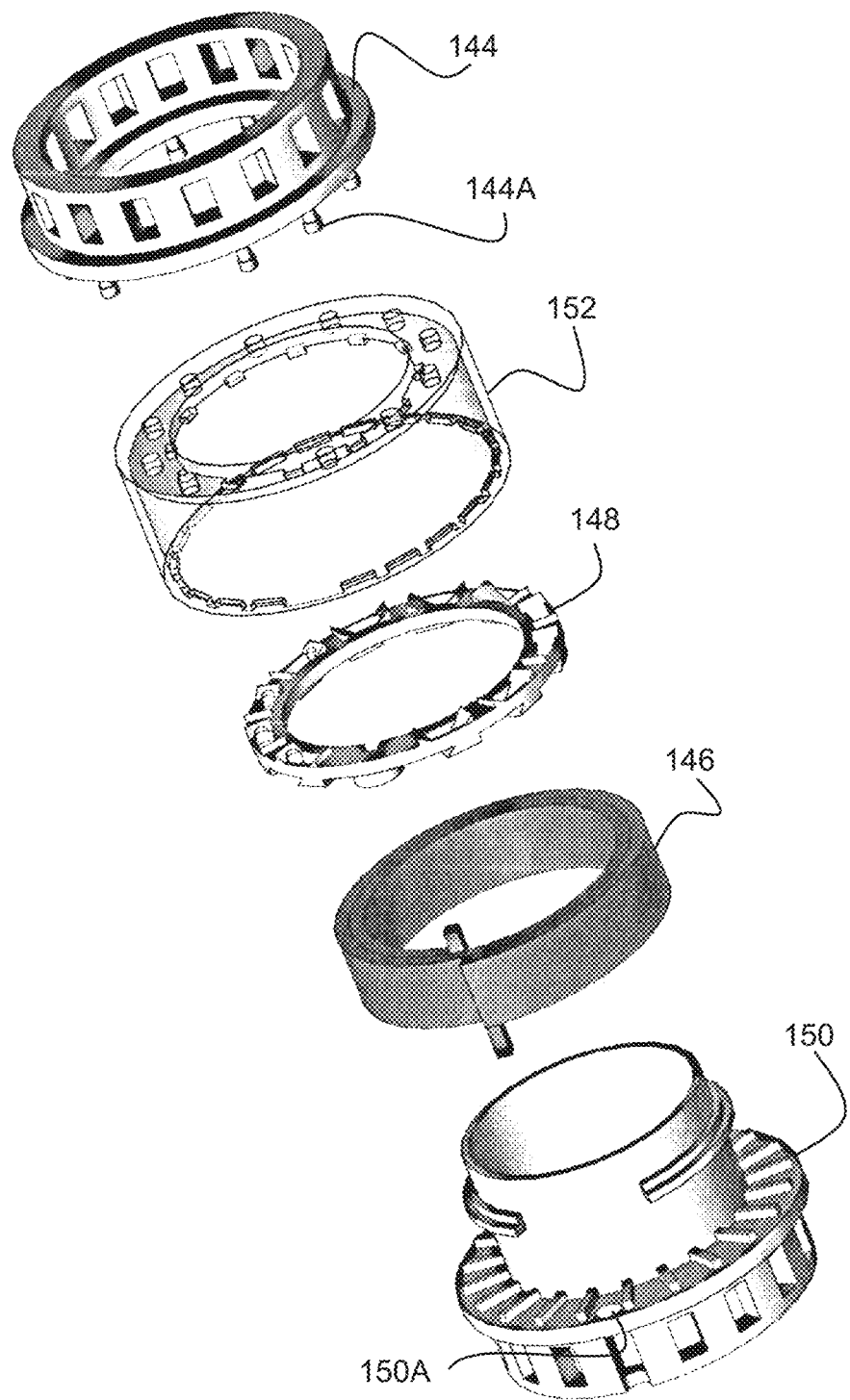
Figure 26:
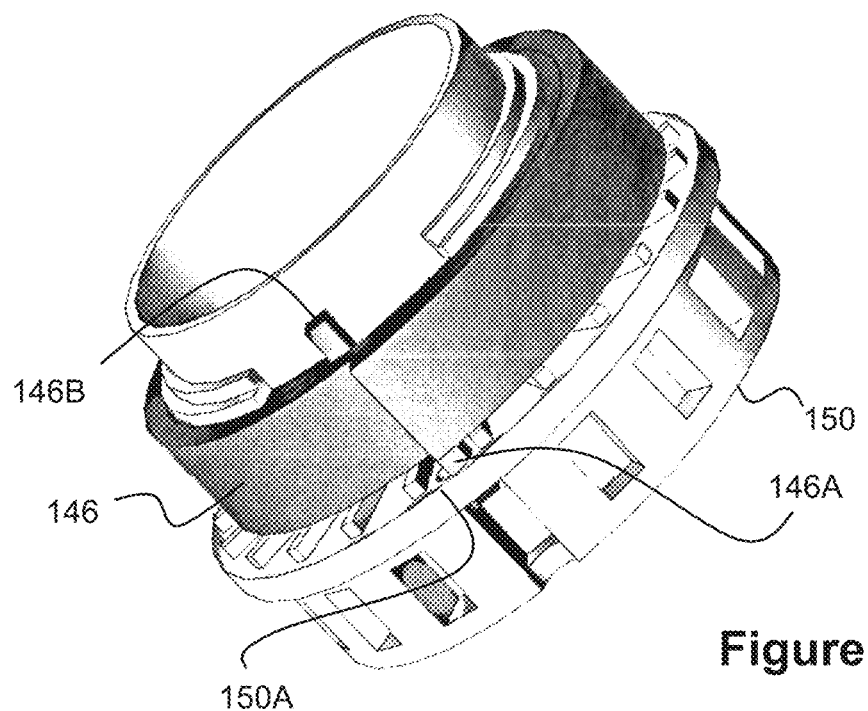
Figure 27:
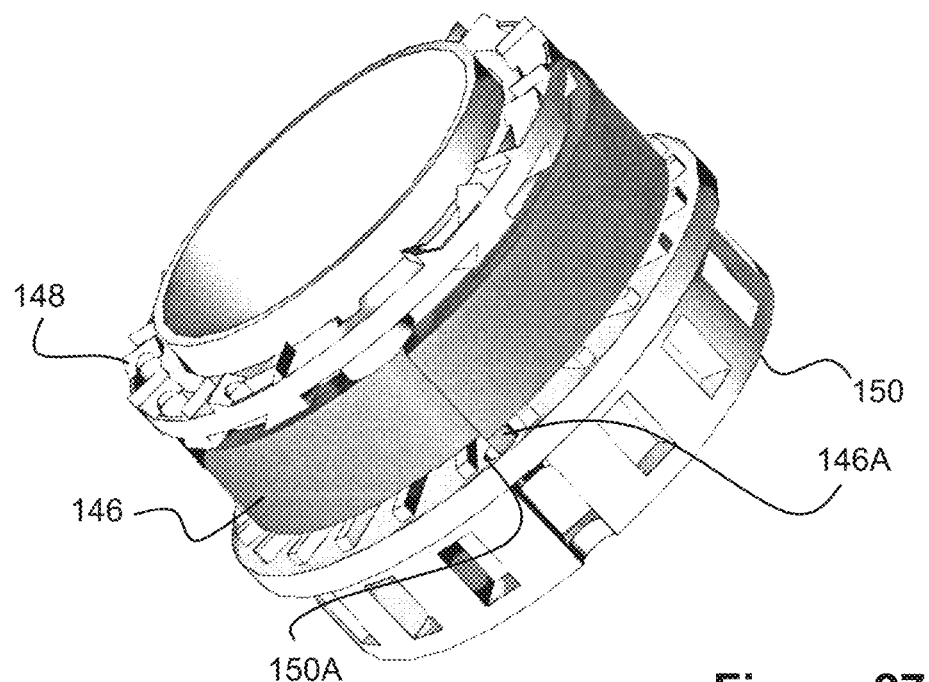
Figure 28:
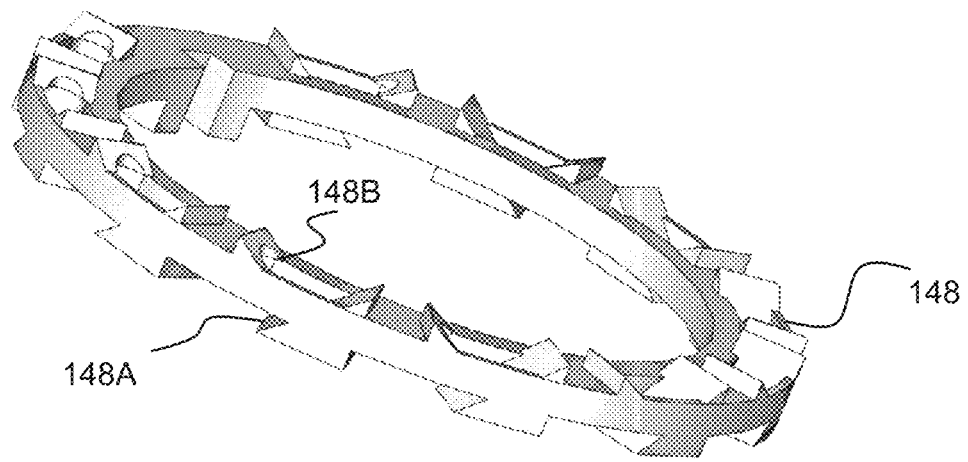

FIGS. 17-19 illustrate another embodiment of a catheter 110 having a tip portion 58 that detaches from a proximal portion 59 via mechanical release mechanism. Specifically, the catheter 110 includes one or more pistons 114 having a pin 116 that moves outward to disengage the mechanical release mechanism. In one example, the mechanical release mechanism includes a hook portion 116A on the distal end of the pin 116 that can be moved from a latched position (FIG. 17) to an unlatched position (FIG. 18). However, it should be understood that a variety of different latching mechanisms can be used with the piston 114.

FIG. 19 illustrates one possible embodiment of the piston 114 in which a pressure-resistant housing 122 and cap 120 contain a material 124 that expands when heated. The material 124 can be any wax, oil, or similar material with a high enough coefficient of expansion to cause movement of the piston 114. In another example, the material 124 can be mercury, ethanol, or other materials with relatively high coefficients of expansion. When the heater coil 112 is activated, it heats up the pistons 114, causing the material 124 to expand within the housing 122, thereby pushing the pin 116 at least partially out of the housing 122.

FIGS. 20-22 illustrate another embodiment of a catheter 130 having a tip portion 58 that detaches from a proximal portion 59 via mechanical release mechanism 132. Specifically, the release mechanism 132 includes a proximal ring 134 and a distal ring 136 that are positioned against each other and are connected or held together via a plurality of tether members or filaments 138. As best seen in the cross sectional view of the ring in FIG. 21, the rings 134 and 136 initially have a generally concave shape relative to each other (e.g., forming a cross sectional oval between each other). However, when the rings 134 and 136 are heated, either by direct application of current to the rings or by an adjacent heater coil, the rings 134 and 136 bend in opposite directions to form convex shapes (FIG. 22). This shape change generally increases the distance of the ends of the rings from each other, where the tether members 138 are connected, thereby fracturing or breaking the tether members 138 and allowing the distal portion 58 of the catheter 130 to be disconnected from the proximal portion 59.

In one embodiment, the temperature bending behavior of the rings 134 and 136 can be created by using a bi-metal design (i.e., a first metal on a first side of the rings and a second, different metal on the second sides of the rings). In another embodiment, the bending behavior of the rings 134 and 136 can be created by using a material capable of Martensite/Austenite transitions. For example, the rings 134, 136 can be composed of Nitinol having a relatively high Austenite finish temperature, such that when current is applied to the rings or a heater coil is activated, the rings 134, 136 transition to their Austenite phase, thereby changing shape, as well.

FIGS. 23-33 illustrate another embodiment of a catheter 140 having a tip portion 58 that detaches from a proximal portion 59 via mechanical release mechanism 142. The mechanical release mechanism 142 preferably includes a heat-activated spring member 146 that maintains the mechanism 142 in a locked state during normal, operational temperatures (e.g., body temperature), but changes shape when heated, either by direct application of current or via an adjacent heater coil, to cause the mechanism 142 to unlock, thereby releasing the distal tip portion 58.

In one embodiment, the temperature bending behavior of the spring member 146 can be created by using a bi-metal design (i.e., a first metal on a first side of the spring member 146 and a second, different metal on the second side of the spring 146). In another embodiment, the shape-changing behavior of the spring member 146 can be created by using a material capable of Martensite/Austenite transitions. For example, the spring member 146 can be composed of Nitinol having a relatively high Austenite finish temperature, such that when current is applied to the spring or a heater coil is activated, the spring member 146 transitions to its Austenite phase, thereby changing shape, as well.

The spring member 146 of the mechanical release mechanism 142 is located on and around a base portion 150. The spring member 146 is further anchored in place on the base portion 150 by a first elongated anchor member 146A at one of its ends, extending into aperture 150A (best seen in FIG. 26). The spring member 146 also includes a second elongated anchor member 146B that extends into an aperture within the locking ring 148 (best seen in FIGS. 27 and 28). In this respect, the spring member 146 maintains the locking ring 148 in a first rotational position relative to the base portion 150 during normal operating temperatures (e.g., body temperature) and rotates the locking ring 148 when heated (via applied current or heater coil).

Figure 29:
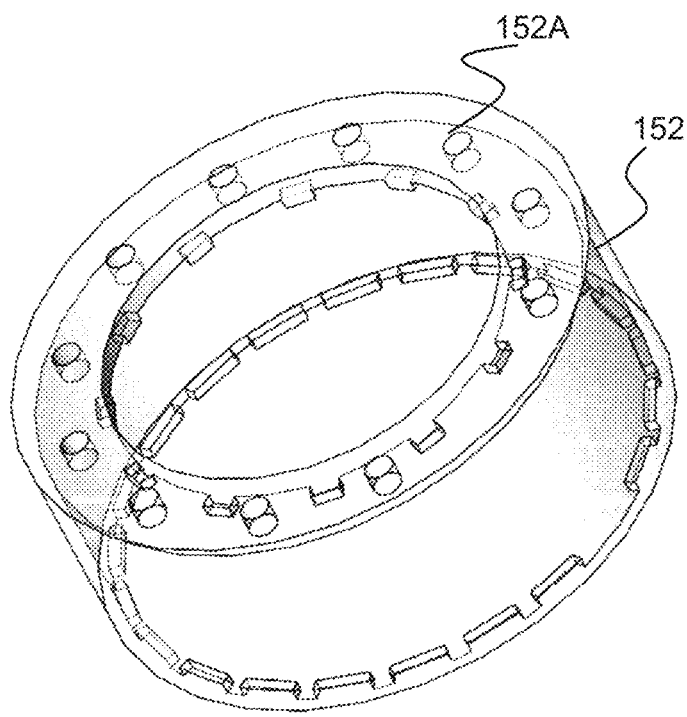
Figure 30:
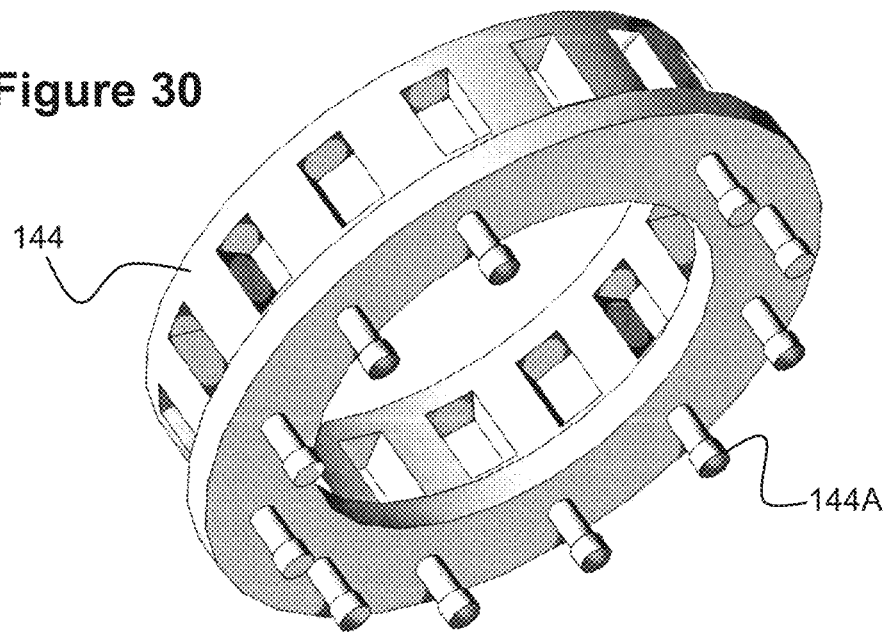

The base portion 150, spring member 146, and locking ring 148 are all preferably contained within an outer housing member 152, which helps maintain the axial positions of these members relative to each other. As best seen in FIG. 29, the outer housing member 152 includes a plurality of apertures 152A which allow passage of locking pins 144A on the ring 144.

Figure 31:
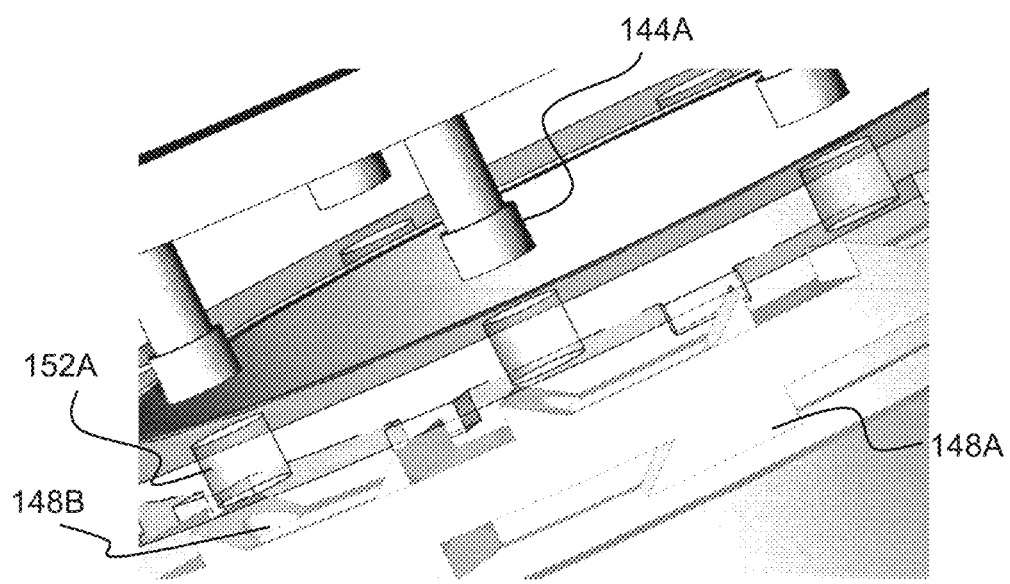
Figure 32:
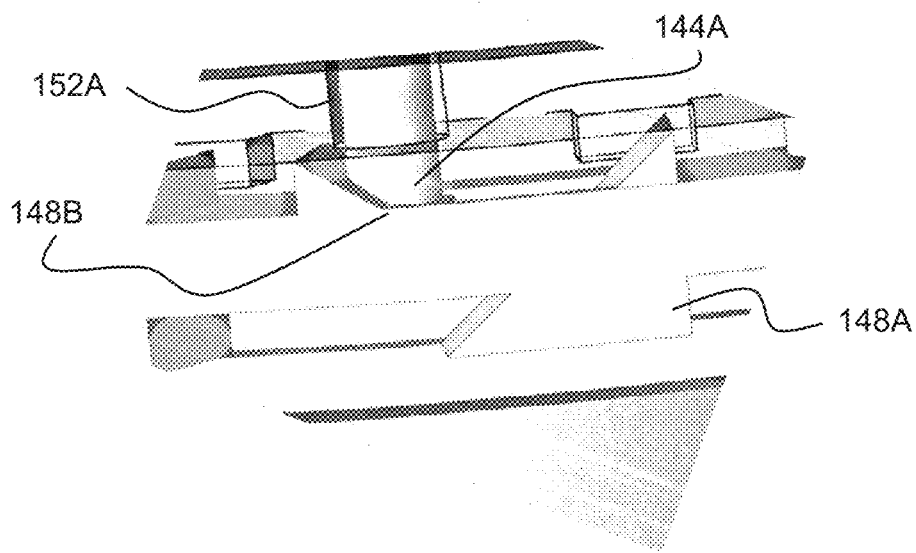
Figure 33:
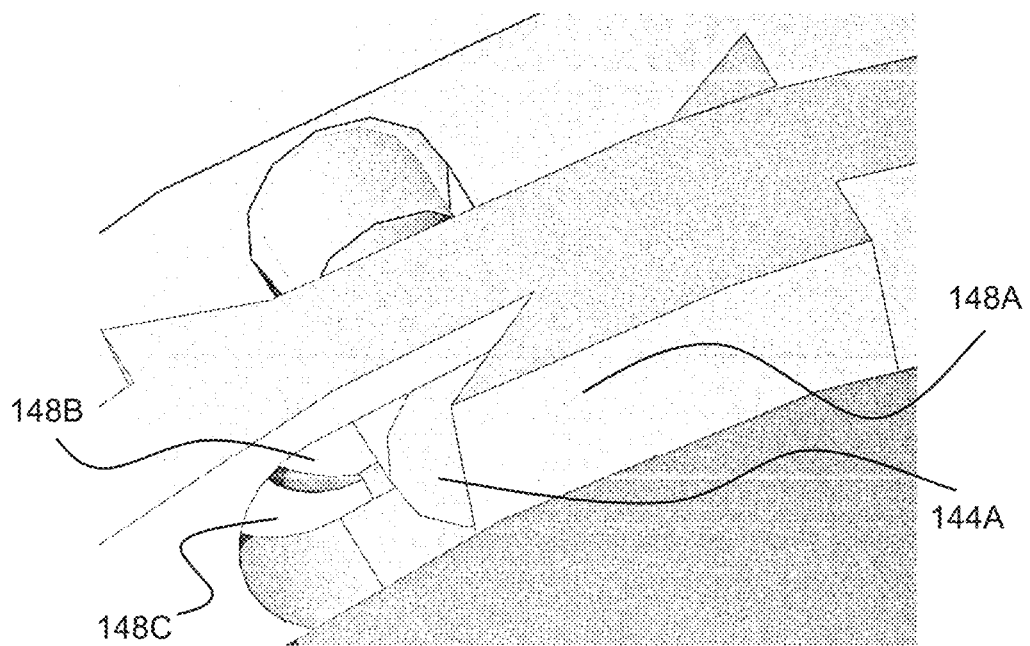

As best seen in FIGS. 31-33, the locking pins 144A pass through apertures 152A and into slots 148B on the locking ring 148. As best seen in FIG. 33, one end of each of the slots 148B include an overhanging portion or lip 148C that is sized and shaped to engage the distal ends of the pins 144A. Specifically, the distal ends of the locking pins 144A have an enlarged diameter relative to the remaining, proximal portions, allowing this distal end to catch on the lip 148C and therefore prevent withdrawal of the pins 144A. Preferably, the spring member 146 is configured to maintain the locking ring 148 in a rotational position that maintains the lip 148C over distal end of the locking pins 144A.

At the opposite end of the slot 148B is a ramped surface 148A which assists in pushing the locking pins 144A out of the slot 148B. Specifically, the ramp 148A is inclined towards the ring 144, such that as the locking ring 148 rotates, the ramp 148A pushes the locking pins 144A axially outward of the housing 152. In this respect, when the spring member 146 is heated, the locking ring 148 rotates to disengage the locking pins 144A with the lip 148C and pushes the pins 144A outward. Since ring 144 and base portion 150 are each attached to either the proximal portion 59 or distal portion 58 of the catheter 140, unlocking the mechanism 142 separates the distal portion 58.

Alternately, rotation of the locking ring 144 of the mechanical release mechanism 142 can be performed via a different mechanism. For example, the piston 114 of FIG. 19 could be fixed to the base 150 or housing 152, as well as the locking ring 144 so as to rotate the ring 144 when heat activates the piston 114.

Figure 34:
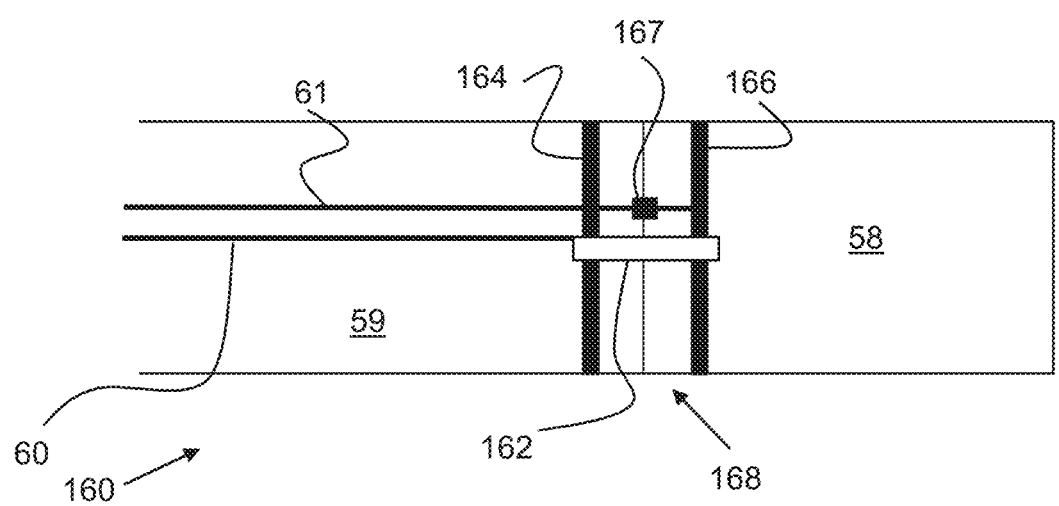
FIG. 34 illustrates another embodiment of a catheter having a detachable tip.

FIG. 34 illustrates another embodiment of a catheter 140 having a tip portion 58 that detaches from a proximal portion 59 via fuse release mechanism 142. Specifically, the portions 58 and 59 can be held together by one or more (e.g., a plurality) of fuse members 162 located near the circumference of the catheter 160.

The fuse members 162 are preferably connected to a proximal ring 164 and a distal ring 166. The proximal ring 164 and/or the proximal end of the fuse members 162 are connected to electrical wire 60, while the distal ring 166 and the distal end of the fuse members 162 are connected to electrical wire 60. Preferably, the electrical wire 61 includes a disconnecting portion 167 that separates when the distal portion 58 separates from the proximal portion 59. For example, the wire 61 can terminate with a first electrode surface that physically presses against a second electrode surface that, in turn, is connected to the remaining wire in the distal portion 58. Hence, electrical communication is provided to the ring 166, but the electrodes provide no retaining force on the distal portion 58.

Preferably, the fuse member 162 is composed of a material that can be fractured or broken without causing enough heat to damage surrounding tissue in a patient (this breaking value is sometimes referred to as the "clearing $I^2t$" value). In one example, the fuse can be composed of an elongated hypotube of gold plated polyimide material.

Figure 35:
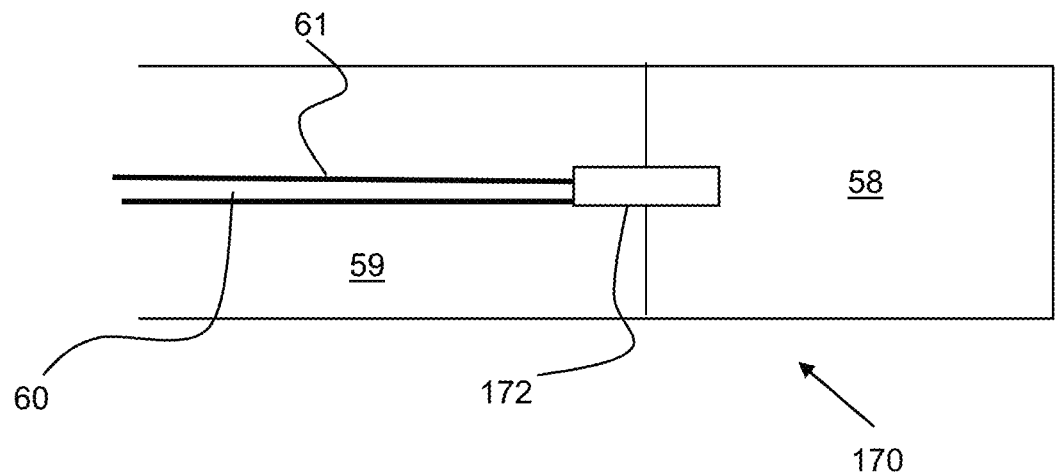
FIGS. 35-36 illustrate another embodiment of a catheter having a detachable tip.
Figure 36:
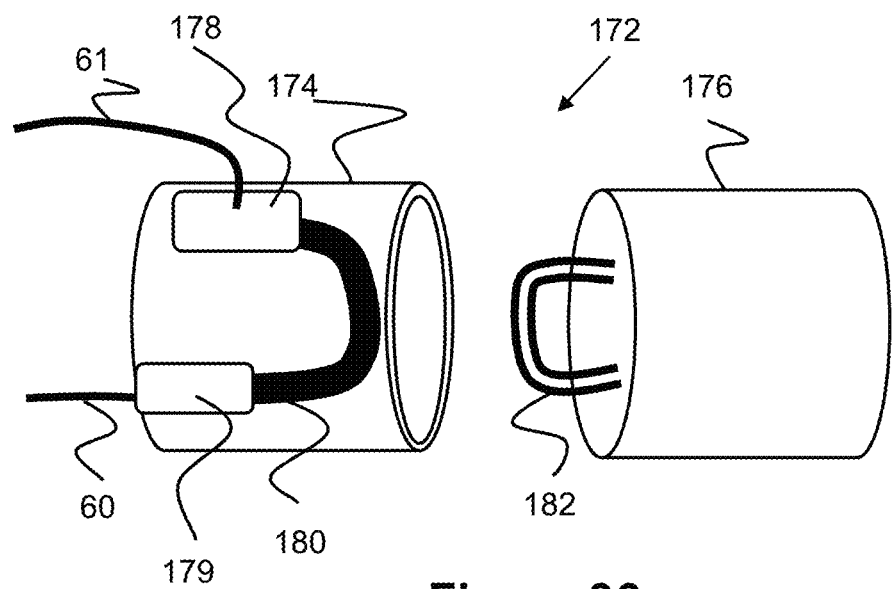

FIGS. 35-36 illustrate another embodiment of a catheter 170 having a tip portion 58 that detaches from a proximal portion 59 via fuse release mechanism 172. Specifically, the portions 58 and 59 can be held together by one or more (e.g., a plurality) of fuse members 172 located near the circumference of the catheter 170, generally similar to the previously discussed catheter 140.

The fuse member 172, best seen in FIG. 36, includes a proximal capsule member 174 having a fuse member 180 fixed within an interior lumen and a distal capsule member 176 having a fixed loop 182 its distal end. When assembled, the fuse member 180 is positioned through the loop 182, locking the two capsule members 176 together.

Preferably, the capsules are composed of or coated with an insulating material, such as ceramic, so as to not conduct current. Current is supplied to the fuse member 180 by two electrical contacts 178, 179, which are insert molded in place. Contact 178 is connected to wire 61 and one end of the fuse member 180, while contact 179 is connected to wire 60 and the other end of the fuse member 180.

As with other embodiments, when detachment is desired, current is applied to wires 60, 61, causing the fuse member 180 to break or fracture. With the loop 182 no longer engaged with the fuse member 176, the distal tip 58 is disconnected from the proximal catheter portion 59.

While one fuse member 172 is discussed, it should be understood that a plurality of fuse members 172 could also be used around the inner circumference of the catheter 170. In such an example, the wires 60, 61 and each of the electrical contacts 178, 179 could each connect to a proximal or distal conducting ring (similar to those in catheter 140).

While the previously described embodiments are described with regard to use as an embolic delivery catheter, these designs can also be used for other purposes. For example, detachable tip balloons, detachable intrasaccular devices, rapid-exchange systems that can detach while still on a guidewire, stent systems, closure devices, neck bridge devices, and coil implants. In this regard, the catheter embodiments of this specification may have a tensile strength of at least 1 pound, a burst pressure of at least 500 psi, and the ability to carry fluid with minimal or no leakage at the tip junction. In one embodiment, the previously described catheters include an internal lumen diameter of about 0.013" and an outer diameter wall of about 0.020", however, the described concepts can be used on larger or smaller sized catheters.

While the previously described embodiments have been depicted as using two relatively straight wires to convey electricity to the distal end of the catheter, it should be understood that other embodiments are possible. For example, current can be carried through a plurality of braided reinforcement wires that extend the length of the catheter. Typically, the metal utilized for the reinforcement braid are either stainless steel or Nitinol, but in this scenario, materials with lower resistance are preferred (e.g., gold, silver, or copper). Additionally, these wires can be formed using a cladding process, such as a copper core having a nickel cladding, a stainless steel core having a gold cladding, or a Nitinol core having a silver cladding. These wires could also have an outer layer of electrical insulation, such as polyimide enamel, parylene, or other suitable substance. These wires may be further grouped into positive and negative bundles, where multiple wires are tied together to increase the current carrying ability and decrease the overall electrical resistance.

It should also be understood that the present invention includes methods of using all of the catheter embodiments described in the present specification and drawings. For example, any of the catheter embodiments can be advanced to a treatment site and embolic material can be deployed from the catheter's distal tip. Should the catheter become stuck in the embolic material, the physician can activate either heat a distal end of catheter to partially melt the embolic material or activate a detachment mechanism to detach a distal end of the catheter. Finally, the catheter can be removed from the patient.

What is claimed is:

1. A detachable tip catheter comprising:
a proximal catheter section;
a distal detachable tip catheter section adjacent the proximal catheter section;
a detachment mechanism connecting the proximal catheter section with the distal detachable tip catheter section; the detachment mechanism comprising one or more pins engaged with a retention structure; and,
electrical wires configured to supply electrical current to the detachment mechanism;
wherein the retention structure moves, without melting, from a first position in which the one or more pins are physically engaged, to a second position in which the one or more pins are disengaged when electrical current is supplied to the detachment mechanism.

2. The detachable tip catheter of claim 1, wherein the electrical current supplied to the detachment mechanism generates heat.

3. The detachable tip catheter of claim 2, wherein the heat generated by the detachment mechanism is produced by a heater coil or by direct application of the current to a spring member.

4. The detachable tip catheter of claim 1, wherein the retention structure maintains a locked state engaging the one or more pins at a first temperature and wherein the retention structure changes to an unlocked state disengaging the one or more pins when at a second temperature that is higher than the first temperature.

5. The detachable tip catheter of claim 1, wherein the retention mechanism comprises a heat-activated spring mechanism.

6. The detachable tip catheter of claim 5, wherein the heat-activated spring mechanism comprises either, 1) a first metal on a first side and a second metal on a second side, or 2) a material having a Martensite/Austenite shape transition.

7. The detachable tip catheter of claim 5, wherein the heat-activated spring mechanism is connected to a locking ring and is further configured to move the locking ring between a first rotational position and a second rotational position.

8. The detachable tip catheter of claim 7, wherein the locking ring has one or more locking ring apertures that are configured to move relative to one or more housing apertures that are adjacent to the one or more locking ring apertures, such that the locking ring engages an enlargement on the one or more pins when in the first rotational position.

9. The detachable tip catheter of claim 1, further comprising a first plurality of apertures and a second plurality of apertures; wherein the first plurality of apertures move relative to the second plurality of apertures to release the one or more pins.

10. The detachable tip catheter of claim 9, wherein the first plurality of apertures are located on a locking ring configured to rotate relative to the second plurality of apertures.

11. The detachable tip catheter of claim 10, further comprising a plurality of ramped surfaces positioned on the locking ring, adjacent to the first plurality of apertures.

12. A catheter comprising:
a proximal catheter portion;
a distal tip portion; and,
a detachment joint releasably connecting the proximal catheter portion with the distal tip portion; the detachment joint comprising a plurality of pins engaged with a retention structure;
wherein the retention structure is configured to move, without melting, from a first position engaging the plurality of pins to a second position releasing engagement of the plurality of pins when electrical current is supplied from the proximal catheter portion to the detachment joint.

13. The catheter of claim 12, wherein the electrical current supplied to the detachment joint generates heat.

14. The catheter of claim 13, wherein the heat generated by the detachment joint is produced by a heater coil or by direct application of the current to a spring member.

15. The catheter of claim 12, wherein the retention structure maintains a locked state engaging the plurality of pins at a first temperature and wherein the retention structure changes to an unlocked state disengaging the plurality of pins when at a second temperature that is higher than the first temperature.

16. The catheter of claim 12, wherein the retention structure comprises a heat-activated spring.

17. The catheter of claim 16, wherein the heat-activated spring mechanism comprises either, 1) a first metal on a first side and a second metal on a second side, or 2) a material having a Martensite/Austenite shape transition.

18. The catheter of claim 16, wherein the heat-activated spring mechanism is connected to a locking ring and is further configured to move the locking ring between a first rotational position and a second rotational position.

19. The catheter of claim 12, further comprising a first plurality of apertures and a second plurality of apertures; wherein the first plurality of apertures move relative to the second plurality of apertures to release the plurality of pins.

20. The catheter of claim 12, wherein the retention structure further comprises a piston.

21. A catheter comprising:
a proximal catheter portion;
a distal tip portion located at a distal end of the proximal catheter portion; and,
a detachment mechanism engaging the proximal catheter portion with the distal tip portion; the detachment portion comprising a plurality of pins engaged with a retention structure;

wherein the retention structure is configured to move, without melting, from a first position engaging the plurality of pins to a second position releasing engagement of the plurality of pins when electrical current is supplied from the proximal catheter portion to the detachment mechanism.

\* \* \* \* \*